US012760193B2

(12) United States Patent
Roeder et al.

(10) Patent No.: US 12,760,193 B2
(45) Date of Patent: Oct. 13, 2026

(54) METHACRYLATED NANOPARTICLES AND RELATED METHOD

(71) Applicants: Ryan Roeder, Granger, IN (US); Lan Li, South Bend, IN (US)

(72) Inventors: Ryan Roeder, Granger, IN (US); Lan Li, South Bend, IN (US)

( * ) Notice: Subject to any disclaimer, the term of this patent is extended or adjusted under 35 U.S.C. 154(b) by 693 days.

(21) Appl. No.: 18/026,818

(22) PCT Filed: Sep. 20, 2021

(86) PCT No.: PCT/US2021/051160
§ 371 (c)(1),
(2) Date: Mar. 16, 2023

(87) PCT Pub. No.: WO2022/061254
PCT Pub. Date: Mar. 24, 2022

(65) Prior Publication Data

US 2023/0323142 A1 Oct. 12, 2023

Related U.S. Application Data

(60) Provisional application No. 63/080,094, filed on Sep. 18, 2020.

(51) Int. Cl.

| | |
|---|---|
| ***C09D 11/101*** | (2014.01) |
| ***A61L 27/04*** | (2006.01) |
| ***A61L 27/16*** | (2006.01) |
| ***A61L 27/34*** | (2006.01) |
| ***A61L 27/50*** | (2006.01) |
| ***C09D 11/033*** | (2014.01) |
| ***C09D 11/037*** | (2014.01) |
| ***C09D 11/107*** | (2014.01) |
| *B82Y 5/00* | (2011.01) |
| *B82Y 40/00* | (2011.01) |

(52) U.S. Cl.

CPC .......... *C09D 11/101* (2013.01); *A61L 27/047* (2013.01); *A61L 27/16* (2013.01); *A61L 27/34* (2013.01); *A61L 27/507* (2013.01); *C09D 11/033* (2013.01); *C09D 11/037* (2013.01); *C09D 11/107* (2013.01); *A61L 2400/12* (2013.01); *B82Y 5/00* (2013.01); *B82Y 40/00* (2013.01)

(58) Field of Classification Search

CPC ....... C09D 11/101; A61L 27/047; A61L 27/34
See application file for complete search history.

(56) References Cited

U.S. PATENT DOCUMENTS

| | | | | |
|---|---|---|---|---|
| 9,840,573 B2 * | 12/2017 | Fujiyama | ................. | G02B 1/04 |
| 2015/0147718 A1 * | 5/2015 | Khakpour | ................ | A61C 5/50 433/81 |

FOREIGN PATENT DOCUMENTS

| | | | | |
|---|---|---|---|---|
| WO | WO-2006045713 A1 * | 5/2006 | ............... | C09D 7/48 |

* cited by examiner

*Primary Examiner* — Andrew S Rosenthal
(74) *Attorney, Agent, or Firm* — McNees Wallace & Nurick LLC

(57) ABSTRACT

A photocrosslinkable agent includes at least one methacrylate-modified nanoparticle that includes a plurality of molecules attached to surface of a nanoparticle. At least a portion of the molecules includes a molecule that includes a nanoparticle surface attachment ligand a terminal methacrylate ligand. At least a portion of the molecules may include a second molecule that includes a nanoparticle surface attachment ligand and a hydrophilic terminal ligand, wherein the methacrylate-modified nanoparticle has water solubility that is controlled by the relative amounts of the terminal methacrylate ligand and the hydrophilic terminal ligand. The photocrosslinkable agent may be crosslinked within a polymer network by a one-step process, with minimal disruption to the molecular network or crosslinking density and may be formulated for use as one or more of an imaging contrast agent, a therapeutic, or a reinforcement, a transducer.

20 Claims, 9 Drawing Sheets

METHACRYLATED NANOPARTICLES AND RELATED METHOD

CROSS-REFERENCE TO RELATED APPLICATIONS

This application claims the benefit of U.S. Provisional Patent Application No. 63/080,094, filed Sep. 18, 2020, which is incorporated by reference in its entirety.

FIELD OF THE INVENTION

The field of the invention is agents and methods for photocrosslinking nanoparticles and polymers, particularly polymer structures that are useful for various medical and non-medical applications, and most particularly for implantable hydrogels.

BACKGROUND OF THE INVENTION

Photocrosslinked hydrogels and photopolymerized polymers, such as methacrylate-modified gelatin (gelMA), methacrylate-modified hyaluronic acid (HAMA), methacrylate-modified collagen (colMA), methacrylate-modified alginate (AlgMA), and polyethylene glycol dimethacrylate (PEGDA), polymethyl methacrylate (PMMA), poly(2-hydroxyethyl methacrylate) (HEMA), among others, are widely utilized as tissue engineering scaffolds and drug delivery vehicles due to enabling precision manufacturing (e.g., 3D printing) of (bio)degradable materials with tunable properties, and the incorporation of drugs or sensitive cells and/or biomolecules. However, in the prior art, these materials are often limited by an inability to non-invasively image or monitor their function, rapid release of drugs or biomolecules, and inferior mechanical or biological properties, and among others.

For example, tissue regeneration and/or cell/biomolecule/drug delivery are well-known to be governed by the degradation rate of a scaffold or hydrogel, but there is not yet an established means for noninvasive, longitudinal, and quantitative monitoring of biomaterial degradation. Current practices for evaluating the safety and efficacy of degradable medical devices and tissue engineered medical products (TEMPs) in preclinical testing are invasive, requiring the excision of implants in multiple animals at multiple time points for destructive testing ex vivo (e.g., histology, mechanical testing, etc.). Therefore, preclinical testing is an extremely costly and time-consuming barrier to translation. Clinical assessment of performance is often limited to subjective patient outcomes. Therefore, a widely-applicable means for non-invasive, longitudinal, and quantitative monitoring of a scaffold or hydrogel—including post-operative surgical placement, degradation, and therapeutic release—would be transformative for both clinical assessment and preclinical development of medical devices and TEMPs.

In another example, drug delivery from implantable hydrogels and scaffolds is often limited by inefficient delivery which leads to poor outcomes, adverse side effects, and high treatment costs. In current clinical delivery vehicles drugs, growth factors, proteins, mRNA and other biomolecules are physisorbed within an hydrogel or scaffold which invariably results in rapid, burst release. After burst release, molecules rapidly dissociate from the scaffold, diffuse away from the target site, and are metabolized. Thus, the majority of the dose is ineffective. This problem in turn leads to the use of higher doses which may be less safe. Thus, a more efficient approach for delivering drugs and biomolecules is needed to improve clinical outcomes and reduce treatment costs.

In another example, scaffolds and hydrogels are widely used for regenerating tissues. However, polymeric scaffolds and hydrogels are often limited by weak mechanical properties such that the implant may be damaged by surgical handling and restricted to non-load bearing or confined sites. Moreover, mechanical fixation of the implant using pins, screws and the like is not possible. Another limitation is that the polymer scaffold or hydrogel alone may lack bioactivity to stimulate a favorable tissue response.

The incorporation of nanoparticles in polymeric hydrogels, scaffolds, and biomaterials, offers a means to overcome the above limitations in the prior art. When integrated within hydrogels and tissue engineering scaffolds, nanoparticles may function as a mechanical reinforcement, a bioactive agent, a drug carrier or delivery vehicle, a transducer for remotely triggering drug release, a contrast agent for imaging, and/or a diagnostic imaging probe for noninvasively monitoring drug release or degradation.

Nanoparticles exhibit advantageous physical interactions with radiation (or photons) at wavelengths across the electromagnetic spectrum, as well as with electrons. These interactions—including absorption, emission, surface plasmon resonance, scattering, and transmission—may enable any number of functionalities for signal transduction, diagnostic imaging, and sensing. Nanoparticles also offer an attractive vehicle for drug delivery systems due to enabling an improved drug payload, solubility, stability, biodistribution, pharmacokinetics and targeting compared to free drugs. Moreover, nanoparticles also offer opportunities for combined therapeutic and diagnostic (theranostic) function. Finally, nanoparticles provide powerful means to improve mechanical properties and provide bioactivity in scaffolds and hydrogels, while possibly mimicking the extracellular matrix of tissues. Nanoparticles are known to support the attachment and proliferation of precursor and progenitor cells.

The method by which nanoparticles are integrated within a hydrogel or scaffold is crucial for achieving the desired functionality. In the prior art, nanoparticles have been incorporated within hydrogels and scaffolds by physical and chemical means.

In physical incorporation, nanoparticles are mixed into a prepolymer or oligomer solution and entrapped within the hydrogel or scaffold during crosslinking. Physical incorporation is simple (one-step) and flexible but may suffer from disrupting the hydrogel network and properties, including premature or uncontrolled (burst) release of nanoparticles which limits the drug delivery and inhibit non-invasive imaging and monitoring hydrogel function.

In chemical incorporation, nanoparticles are surface functionalized (a.k.a., surface modified) with ligands that are able to be chemically-coupled to photopolymerizable macromolecules. Chemically-incorporated nanoparticles are immobilized such that their release coincides with hydrolytic or enzymatic degradation of the scaffold or hydrogel for controlled or on-demand drug delivery, prolonged imaging contrast, and more accurate and reliable monitoring of function. However, chemical incorporation of nanoparticles in scaffolds or hydrogels requires modification of both nanoparticle surfaces and prepolymer macromolecules, involving multi-step reactions with potentially undesirable side reactions, prior to photocrosslinking.

The inventors hereof have further recognized that methods known in the art for physical and chemical incorporation of nanoparticles in photocrosslinked hydrogels and scaffolds result in a disrupted hydrogel network and/or reduced crosslinking density. In physical mixing of nanoparticles and prepolymer solutions, nanoparticles are unable to participate in photocrosslinking and thus disrupt the hydrogel network. Chemical-coupling nanoparticles to macromolecules prior to photocrosslinking disrupts hydrogel network and also decreases the crosslinking density.

Thus, simple, and flexible methods are needed for the chemical incorporation of nanoparticles in photocrosslinked hydrogels and materials with minimal disruption of the crosslinked network structure and properties.

The instant disclosure overcomes the deficiencies of the art as noted above.

SUMMARY OF THE INVENTION

In accordance with various embodiments, the disclosure provides a photocrosslinkable agent comprising at least one methacrylate-modified nanoparticle (100) comprising a nanoparticle, and a plurality of molecules attached to surface of the nanoparticle, at least a portion of the plurality of molecules comprising at least a first molecule, the first molecule comprising at least one nanoparticle surface attachment ligand (1) and at least one terminal methacrylate ligand (103).

In a representative embodiment, the photocrosslinkable agent comprises at least one methacrylate-modified nanoparticle comprising a gold nanoparticle; and a plurality of molecules attached to surface of the gold nanoparticle, at least a portion of the plurality of molecules comprising at least a first molecule, the first molecule comprising at least one nanoparticle surface attachment ligand (1) comprising a thiol terminal group, and at least one terminal methacrylate ligand (103). A portion of the plurality of molecules may comprise a second molecule, the second molecule comprising at least one nanoparticle surface attachment ligand (1) comprising a thiol terminal group and at least one hydrophilic terminal ligand (2) comprising a carboxylate terminal group, wherein the methacrylate-modified nanoparticle has water solubility that is controlled by the relative amounts of the first molecule comprising at least one terminal methacrylate ligand (103) and the second molecule comprising the at least one hydrophilic terminal ligand (2) comprising a carboxylate terminal group.

In a representative embodiment, a photocrosslinked composite hydrogel is provided comprising the photocrosslinkable agent which comprises at least one of a plurality of methacrylate-modified gold nanoparticles, wherein at least one of a plurality of methacrylate-modified nanoparticles of the photocrosslinkable agent is photocrosslinked within a plurality of methacrylate-modified macromolecules (107), wherein at least a portion of the plurality of the terminal methacrylate ligands (103) are photocrosslinked with at least a portion of the methacrylate-modified macromolecules (107), the photocrosslinked material comprising a covalent linkage between the photocrosslinked methacrylate-modified nanoparticles and methacrylate-modified macromolecules (107).

In a representative embodiment, method for providing a photocrosslinkable agent includes providing a gold nanoparticle; providing a first bifunctional molecule (105) (i.e., a nanoparticle surface attachment molecule) comprising at least a first nanoparticle surface attachment ligand (1) comprising a thiol terminal group that is attached to a surface of the gold (Au) nanoparticle, and at least one hydrophilic terminal ligand (2) comprising a carboxylate terminal group capable of covalent linking to a terminal ligand of a second bifunctional molecule (106) (i.e., a terminal methacrylate molecule); providing the second bifunctional molecule (106) comprising at least one terminal methacrylate (MA) ligand (103) and at least one terminal coupling ligand (4) comprising an amine terminal group and capable of covalent linking to the hydrophilic terminal ligand (2) comprising a carboxylate terminal group of the first molecule; and covalently linking the hydrophilic terminal ligand (2) comprising a carboxylate terminal group of the first bifunctional molecule to the terminal coupling ligand (4) comprising an amine terminal group of the second bifunctional molecule, in the presence of 1-ethyl-3-(3-dimethylaminopropyl) carbodiimide hydrochloride (EDC) and N-hydroxysuccinimide or N-hydroxysulfosuccinimide (NHS) in alcohol, wherein the molar ratio of Au:EDC:NHS:MA is in the range of 100:15:6:6 to 1:50:20:20.

In some embodiments, the at least one nanoparticle surface attachment ligand (1) includes, but is not limited to, thiols, amines, alcohols, silanes, carboxylates, phosphonates, and combinations thereof.

In some embodiments, a portion of the plurality of molecules comprise a second molecule, the second molecule comprising at least one nanoparticle surface attachment ligand (1) and at least one hydrophilic terminal ligand (2).

In some embodiments, the methacrylate-modified nanoparticle (100) has water solubility that is controlled by the relative amounts of the terminal methacrylate ligand (103) and the hydrophilic terminal ligand (2).

In some embodiments, the at least one hydrophilic terminal ligand (2) includes, but is not limited to, thiols, amines, alcohols, carboxylates, silanes, phosphonates, acrylates, epoxides, and combinations thereof.

In some embodiments, the photocrosslinkable agent is formulated for a use including but not limited to an imaging contrast agent, a therapeutic, a reinforcement, a transducer, and combinations thereof.

In some embodiments, the nanoparticles have a shape that includes, but is not limited to, nanospheres, nanorods, nanoplates, nanoshells, nanotubes, nanocages, nanostars, and combinations thereof.

In some embodiments, the nanoparticles are composed of at least one material selected from the group consisting of a metal, a ceramic (e.g., an oxide), a semiconductor, a polymer, and combinations thereof.

In some embodiments, the nanoparticles are composed of a combination of at least two materials selected from the group consisting of a metal, a ceramic (e.g., an oxide), a semiconductor, and a polymer, each material forming at least a portion of the nanoparticle, wherein the nanoparticles have a core-shell structure or a Janus structure.

In some embodiments, the nanoparticles are composed of a metal or a metal portion, the metal or metal portion of the nanoparticle includes, but is not limited to, magnesium, aluminum, titanium, vanadium, chromium, manganese, iron, cobalt, nickel, nitinol, copper, zinc, selenium, zirconium, molybdenum, palladium, silver, gadolinium, tantalum, tungsten, iridium, platinum, gold, bismuth, and alloys and combinations thereof.

In some embodiments, the nanoparticles are composed of a ceramic or a ceramic portion, the ceramic or ceramic portion of the nanoparticle includes, but is not limited to, boron nitride, magnesium oxide, aluminum oxide, aluminum nitride, silicon dioxide, silicon nitride, titanium dioxide, titanium carbide, hematite or iron(III) oxide, magnetite or iron(II,III) oxide, copper oxide, zinc oxide, strontium titanate, zirconium oxide, cerium oxide, gadolinium oxide, tantalum oxide, barium titanate, barium sulfate, hafnium oxide, tungsten oxide, oxides comprising rare earth elements, hydroxyapatite, calcium-deficient hydroxyapatite, carbonated calcium hydroxyapatite, beta-tricalcium phosphate, alpha-tricalcium phosphate, amorphous calcium phosphate, octacalcium phosphate, tetracalcium phosphate, biphasic calcium phosphate, anhydrous dicalcium phosphate, dicalcium phosphate dihydrate, anhydrous monocalcium phosphate, monocalcium phosphate monohydrate, calcium silicates, calcium aluminates, calcium carbonate, calcium sulfate, zinc phosphate, zinc silicates, aluminosilicates, zeolites, bioglass 45, bioglass 52S4.6, other glasses and glass-ceramics comprising silica, calcium oxide, soda, alumina, and/or phosphorus pentoxide, and combinations thereof.

In some embodiments, the nanoparticles are composed of a semiconductor or a semiconductor portion, the semiconductor or semiconductor portion of the nanoparticle includes, but is not limited to, silicon, graphene, zinc oxide, zinc sulfide, zinc selenide, gallium arsenide, cadmium oxide, cadmium sulfide, cadmium selenide, and combinations thereof.

In some embodiments, the nanoparticles are composed of a polymer or a polymer portion, the polymer or polymer portion of the nanoparticle includes, but is not limited to, polyaryletherketone (PAEK), polyetheretherketone (PEEK), polyetherketonekteone (PEKK), polyetherketone (PEK), polytetrafluoroethylene (PTFE) polyethylene, high density polyethylene (HDPE), ultra-high molecular weight polyethylene (UHMWPE), low density polyethylene (LDPE), polyethylene oxide (PEO), polyethylene terephthalatepolyurethane (PET), polypropylene, polypropylene oxide (PPO), polysulfone, polyethersulfone, polyphenylsulfone, poly(vinyl chloride) (PVC), polyoxymethylene, polyacrylonitrile (PAN), polystyrene, poly(vinyl alcohol) (PVA), poly(DL-lactide) (PDLA), poly(L-lactide) (PLLA), poly(glycolide) (PGA), poly(ε-caprolactone) (PCL), poly(dioxanone) (PDO), poly(glyconate), poly(hydroxybutyrate) (PHB), poly (hydroxyvalerate (PHV), poly(orthoesters), poly(carboxylates), poly(propylene fumarate), poly(phosphates), poly (carbonates), poly(anhydrides), poly(iminocarbonates), poly (phosphazenes), polyimides, polyamides, polysiloxanes, polyphosphates, citric-acid based polymers, polyacrylics, polymethylmethacrylate (PMMA), bisphenol A-glycidyl methacrylate (bis-GMA), tri(ethylene glycol) dimethacrylate (TEG-DMA), poly(2-hydroxyethyl methacrylate) (HEMA), poly(acrylic acid) (PAA), polyethylene glycol (PEG), polysaccharides, gelatin, collagen, alginate, chitosan, dextran, carboxymethyl cellulose, polypeptides, copolymers thereof, and combinations thereof.

In accordance with various embodiments, the disclosure also provides a photocrosslinkable ink for forming a material or structure, comprising: a suitable solvent at least one of a plurality of methacrylate-modified nanoparticles, the at least one of a plurality of methacrylate-modified nanoparticles (100) comprising a nanoparticle; a plurality of molecules attached to the surface of the nanoparticle, at least a portion of the plurality of molecules comprising at least a first molecule comprising at least one nanoparticle surface attachment ligand (1) and at least one terminal methacrylate ligand (103); optionally a plurality of methacrylate-modified macromolecules (107); and a photoinitiator In some embodiments, the plurality of methacrylate-modified macromolecules (107) includes, but is not limited to, polymers, oligomers or a combination thereof including but not limited to, gelatin-methacrylate (gelMA), collagen-methacrylate (colMA), alginate-methacrylate (algMA), hyaluronic acid-methacrylate (HAMA), dextran-methacrylate (dexMA), chitosan-methacrylate (chiMA), chondroitin sulfate-methacrylate (CSMA), heparin-methacrylate (hepMA), carboxymethyl cellulose-methacrylate (CMCMA), polyethylene glycol dimethacrylate (PEGDA), polyurethane-methacrylate, polyacrylic acid (PAA), polymethyl methacrylate (PMMA), poly(2-hydroxyethyl methacrylate) (HEMA), bisphenol A-glycidyl methacrylate (bis-GMA), tri(ethylene glycol) dimethacrylate (TEG-DMA), diethyleneglycol diacrylate (DEGDA), and combinations thereof.

In some embodiments, the solvent is water, the at least one of a plurality of methacrylate-modified nanoparticles (100) further comprising at least a second molecule, the second molecule comprising at least one nanoparticle surface attachment ligand (1) and at least one hydrophilic terminal ligand (2).

In some embodiments, the at least one of a plurality of methacrylate-modified nanoparticles (100) has water solubility that is controlled by the relative amounts of the terminal methacrylate ligand (103) and the hydrophilic terminal ligand (2).

In some embodiments, the photocrosslinkable ink comprises a plurality of methacrylate-modified nanoparticles, wherein at least a portion of the plurality of methacrylate-modified nanoparticles (100) are photocrosslinked with at least a portion of the plurality of methacrylate-modified macromolecules (107), resulting in a covalent linkage (109) between at least a portion of the nanoparticles and methacrylate-modified macromolecules (107), prior to photocrosslinking all the methacrylate-modified nanoparticles (100) and methacrylate-modified macromolecules (107).

In accordance with various embodiments, the disclosure also provides a photocrosslinked material comprising the photocrosslinkable agent.

In some embodiments, the photocrosslinked material comprises at least one of a plurality of methacrylate-modified nanoparticles, wherein at least one of a plurality of methacrylate-modified nanoparticles (100) of the photocrosslinkable agent is photocrosslinked within a plurality of methacrylate-modified macromolecules (107), wherein at least a portion of the plurality of the terminal methacrylate ligands (103) are photocrosslinked with at least a portion of the methacrylate-modified macromolecules (107), the photocrosslinked material comprising a covalent linkage between the photocrosslinked methacrylate-modified nanoparticles (100) and methacrylate-modified macromolecules (107).

In some embodiments, the photocrosslinked material exhibits at least one or more properties that includes, but is not limited to, crosslinking density, rheology, mechanical stiffness, mechanical strength, swelling, degradation kinetics, and any combination thereof, and wherein at least one or more of the properties are not substantially altered by the presence of the photocrosslinkable agent as compared to a photocrosslinked product formed by photocrosslinking the methacrylate-modified macromolecules (107) in the absence of the photocrosslinkable agent.

In accordance with various embodiments, the disclosure also provides a photocrosslinked material comprising the photocrosslinkable agent wherein the photocrosslinkable agent is photocrosslinked. In some embodiments, at least a portion of the plurality of the terminal methacrylate ligands (103) are photocrosslinked between nanoparticles (101), resulting in a covalent linkage (109) between methacrylate-modified nanoparticles (100).

In accordance with various embodiments, the disclosure also provides a method for providing a photocrosslinkable agent, the method comprising providing a nanoparticle, providing a first bifunctional molecule (105) comprising at least one nanoparticle surface attachment ligand (1) that is attached to a surface of the nanoparticle, and at least one terminal ligand comprising a hydrophilic terminal ligand (2) capable of covalent linking to a terminal ligand of another molecule, providing a second bifunctional molecule (106) comprising at least one terminal methacrylate ligand (103) and at least one terminal ligand comprising a coupling ligand (4) capable of covalent linking to the hydrophilic terminal ligand (2) of the first molecule, and covalently linking the hydrophilic terminal ligand (2) of the first molecule to the coupling ligand (4) of the second molecule, optionally in the presence of a coupling agent or catalyst.

In some embodiments, the hydrophilic terminal ligand (2) of the first molecule is hydrophilic, and wherein covalent linking to the coupling ligand (4) of the second molecule is carried out under conditions that result in incomplete conversion of the hydrophilic terminal coupling ligands (2) such that the nanoparticle is surface functionalized with a conjugated molecule comprising a nanoparticle surface attachment ligand (1) and a terminal methacrylate ligand (103), and the first molecule comprising the nanoparticle surface attachment ligand (1) and the hydrophilic terminal ligand (2), and wherein the methacrylate-modified nanoparticle (100) has a water solubility that is controlled by the relative amounts of the conjugated molecule and the first molecule.

In accordance with various embodiments, the disclosure also provides a method of forming a photocrosslinked material comprising, providing the photocrosslinkable ink and photocrosslinking the provided photocrosslinkable ink.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

Figure 1:
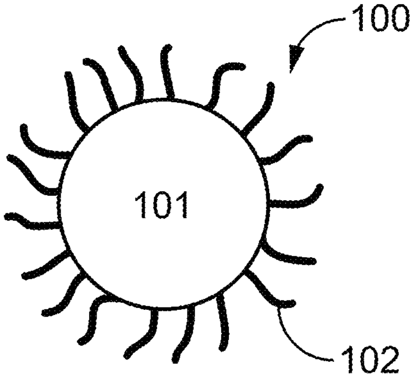
FIG. 1 shows a graphical representation of an embodiment of the invention, including a nanoparticle (101) surface functionalized with multiple molecules (102)

The general inventive concepts will now be described with occasional reference to the exemplary embodiments of the invention. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

| | |
|---|---|
| 100 | (surface functionalized nanoparticle) methacrylate-modified nanoparticle |
| 101 | nanoparticle |
| 102 | methacrylate ligand molecule |
| 103 | methacrylate ligand |
| 1 | nanoparticle surface attachment ligand |
| 2 | hydrophilic terminal ligand |
| 3 | reactive terminal ligand |
| 104 | hydrophilic ligand molecule (includes a hydrophilic terminal ligand (2) opposite a nanoparticle surface attachment ligand (1)) |
| 105 | first bifunctional molecule |
| 106 | second bifunctional molecule |
| 4 | coupling ligand |
| 107 | plurality of methacrylate-modified macromolecules |
| 108 | optional photoinitiator |
| 109 | covalent linkage between the methacrylate-modified nanoparticle and methacrylate-modified macromolecule formed by photocrosslinking |
| 110 | photocrosslinked hydrogel or polymer with covalently-linked in nanoparticles in an otherwise undisrupted hydrogel or polymer network |
| 111 | absence of coupling between the nanoparticle and methacrylate-modified macromolecule after photocrosslinking |
| 112 | photocrosslinked hydrogel or polymer with encapsulated nanoparticles |
| 114 | covalent linkage between the methacrylate-modified nanoparticle and methacrylate-modified macromolecule formed before photocrosslinking |
| 115 | photocrosslinked hydrogel or polymer with covalently-linked nanoparticles in a disrupted hydrogel or polymer network |

DETAILED DESCRIPTION OF THE INVENTION

The inventors have provided a photocrosslinkable agent that solves many of the deficiencies in the art. The photocrosslinkable agent includes at least one methacrylate-modified nanoparticle that includes a plurality of molecules attached to surface of a nanoparticle. At least a portion of the molecules includes a molecule that includes a nanoparticle surface attachment ligand and a terminal methacrylate ligand. At least a portion of the molecules may include a second molecule that includes a nanoparticle surface attachment ligand and a hydrophilic terminal ligand, wherein the methacrylate-modified nanoparticle has water solubility that is controlled by the relative amounts of the terminal methacrylate ligand and the hydrophilic terminal ligand.

The inventors have shown that the photocrosslinkable agent may be crosslinked within a polymer network by a one-step process, with minimal disruption to the molecular network or crosslinking density as compared with the same polymer network in the absence of the methacrylate-modified nanoparticles. In sharp contrast, comparable prior art solutions do not perform as well. As more specifically described herein below, the photocrosslinkable agent has been shown to perform in an improved manner relative to prior art solutions wherein in some prior art examples, processed, nanoparticles are unable to form covalent linkages with macromolecules in a polymer network, or the prior art NP-polymer networks require more than a single reaction step and result in disruption to the molecular network or crosslinking density.

As further described herein, in various embodiments, the photocrosslinkable agent, may be formulated in an ink or other reagent for use as one or more of an imaging contrast agent, a therapeutic, or a reinforcement, a transducer.

Photocrosslinkable Agent

Figure 2:
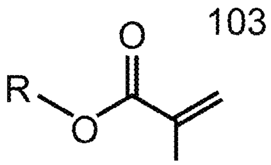
FIG. 2 shows a graphical representation of the molecular structure of a terminal methacrylate ligand (103)
Figure 3:
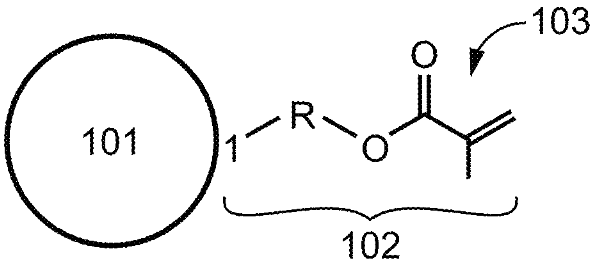
FIG. 3 shows a graphical representation of an embodiment of the invention, including a nanoparticle (101) surface functionalized with one of the multiple molecules (102) that are depicted in FIG. 1 comprising a first molecule that includes a nanoparticle surface attachment ligand (1) and a terminal methacrylate ligand (103)

According to various embodiments, the disclosure provides a photocrosslinkable agent comprising at least one methacrylate-modified nanoparticle (100) comprising a nanoparticle, and a plurality of molecules (102) attached to surface of the nanoparticle. In the various embodiments, at least a portion of the plurality of molecules include at least a first molecule comprising at least one nanoparticle surface attachment ligand (1) and at least one terminal methacrylate ligand (103). Referring now to the drawings, FIG. 1 shows a graphical representation of an embodiment of the invention, including a nanoparticle (101) surface functionalized with multiple molecules comprising at least a first molecule comprising a methacrylate ligand molecule (102). FIG. 2 shows a graphical representation of the molecular structure of a terminal methacrylate ligand (103). And FIG. 3 shows a graphical representation of an embodiment of the invention, including a nanoparticle (101) surface functionalized with one of the multiple molecules (102) that are depicted in FIG. 1 comprising the methacrylate ligand molecule (102) that includes a nanoparticle surface attachment ligand (1) and the molecular structure of a terminal methacrylate ligand (103). As commonly used in the art, R denotes any suitable molecular structure between the terminal ligands.

Figure 4:
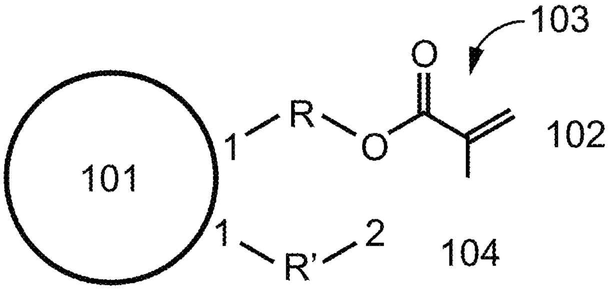
FIG. 4 shows a graphical representation of an embodiment of the invention, including a nanoparticle (101) surface functionalized with two of the multiple molecules (102) that are depicted in FIG. 1, the two molecules comprising a first molecule that includes a nanoparticle surface attachment ligand (1) and a terminal methacrylate ligand (103) opposite the nanoparticle surface attachment ligand (1), and a second molecule that includes a nanoparticle surface attachment ligand (1) and a hydrophilic terminal ligand (2) opposite the nanoparticle surface attachment ligand (1)

In some embodiments, at least a portion of the plurality of molecules of the photocrosslinkable agent comprise at least a second molecule comprising at least one nanoparticle surface attachment ligand (1) and at least one hydrophilic terminal ligand (2). Referring again to the drawings, FIG. 4 shows a graphical representation of an embodiment of the invention, including a nanoparticle (101) surface functionalized with two of the multiple molecules (102) that are depicted in FIG. 1, the two molecules comprising a specific molecule that includes a nanoparticle surface attachment ligand (1) and the molecular structure of a terminal methacrylate ligand (103) opposite the nanoparticle surface attachment ligand (1), and specific molecule that includes a nanoparticle surface attachment ligand (1) and a hydrophilic terminal ligand (2) opposite the nanoparticle surface attachment ligand (1). Referring still to FIG. 4, the first molecule (102) includes a terminal methacrylate ligand (103) opposite a ligand (1) capable of attaching to the nanoparticle surface. The second molecule (104) includes a hydrophilic terminal ligand (2) opposite a ligand (1) capable of attaching to the nanoparticle surface. The relative amount of hydrophobic methacrylate-terminated molecules and molecules with a hydrophilic terminal ligand may be tailored to control the aqueous solubility of the surface modified nanoparticles. As commonly used in the art, R or R' denote any suitable molecular structure between the terminal ligands.

According to embodiments of the method of making the photocrosslinkable agent, as described herein below, the methacrylate-modified nanoparticle (100) comprising the first and second molecules is formed by a reaction that includes a plurality of bifunctional molecules.

As used herein, the term "bifunctional molecule" refers to a molecule that has at least one functional group or ligand on each of two opposite terminal ends, or a molecule that has at least one functional group or ligand on a first end that is bound to a nanoparticle and at least one functional group or ligand on an opposite terminal end. Accordingly, in some embodiments, a bifunctional molecule includes two chemically functional groups or ligand on opposite ends of the molecule. In some embodiments, a bifunctional molecule includes one or more chemically functional groups or ligands on each of opposite ends. And in some embodiments, a bifunctional molecule includes at least two or more chemically functional moieties on each of opposite ends. Further, any molecule as described herein, except as may be otherwise expressly stated as comprising only the end functional groups or ligand, and including but not limited to a bifunctional molecule, may include intervening groups and/or chemical structures within the molecule and between the opposite ends.

As used herein, the term "photocrosslinking" is commonly used interchangeably with "photopolymerization" in the art and is intended to have the same understood meaning.

As used herein, the term "methacrylate" as used in the context of MA-modified nanoparticles (or NPs or molecules) is synonymous with "methacryloyl" which is commonly used in the art. Further, in many embodiments, "acrylate" can also be used in place of "methacrylate" wherein both present the same vinyl group.

Nanoparticles (101)

In accordance with the disclosure, the inventive materials and method include one or a plurality of nanoparticles.

In embodiments, the nanoparticle (101) may be composed of a metal, a ceramic (e.g., oxide, nitride, carbide, etc.), a semiconductor, a polymer, or combinations thereof in a core-shell or Janus structure. As described herein below, any one or combination of the listed materials may be used to provide a nanoparticle for use according to the invention.

The metal or metal portion of the nanoparticle may be composed of any suitable metal or metal alloy including, but not limited to, magnesium, aluminum, titanium, vanadium, chromium, manganese, iron, cobalt, nickel, nitinol, copper, zinc, selenium, zirconium, molybdenum, palladium, silver, gadolinium, tantalum, tungsten, iridium, platinum, gold, bismuth, and combinations thereof. In some particular embodiments, the metal or metal portion of the nanoparticle may be most preferably composed of any one or a combination of noble metals, and in some particular embodiments, one or more of gold, silver, platinum, and palladium.

The ceramic or ceramic portion of the nanoparticle may be composed of any suitable oxide, nitride, carbide or sulfate including, but not limited to, boron nitride, magnesium oxide, aluminum oxide, aluminum nitride, silicon dioxide, silicon nitride, titanium dioxide, titanium carbide, hematite or iron(III) oxide, magnetite or iron(II,III) oxide, copper oxide, zinc oxide, strontium titanate, zirconium oxide, cerium oxide, gadolinium oxide, tantalum oxide, barium titanate, barium sulfate, hafnium oxide, tungsten oxide, other complex oxides, nitrides and carbides, and combinations thereof.

The ceramic or ceramic portion of the nanoparticle may be composed of calcium phosphates and other bioactive compositions including, but not limited to, hydroxyapatite, calcium-deficient hydroxyapatite, carbonated calcium hydroxyapatite, beta-tricalcium phosphate, alpha-tricalcium phosphate, amorphous calcium phosphate, octacalcium phosphate, tetracalcium phosphate, biphasic calcium phosphate, anhydrous dicalcium phosphate, dicalcium phosphate dihydrate, anhydrous monocalcium phosphate, monocalcium phosphate monohydrate, calcium silicates, calcium aluminates, calcium carbonate, calcium sulfate, zinc phosphate, zinc silicates, aluminosilicates, zeolites, bioglass 45, bioglass 52S4.6, other glasses and glass-ceramics comprising silica, calcium oxide, soda, alumina, and/or phosphorus pentoxide, and combinations thereof.

The semiconductor or semiconductor portion of the nanoparticle may be composed of any suitable semiconductor including, but not limited to, silicon, graphene, zinc oxide, zinc sulfide, zinc selenide, gallium arsenide, cadmium oxide, cadmium sulfide, cadmium selenide, and combinations thereof.

The polymer or polymer portion of the nanoparticle may composed of any suitable polymer including, but not limited to, polyaryletherketone (PAEK), polyetheretherketone (PEEK), polyetherketonekteone (PEKK), polyetherketone (PEK), polytetrafluoroethylene (PTFE) polyethylene, high density polyethylene (HDPE), ultra-high molecular weight polyethylene (UHMWPE), low density polyethylene (LDPE), polyethylene oxide (PEO), polyethylene terephthalatepolyurethane (PET), polypropylene, polypropylene oxide (PPO), polysulfone, polyethersulfone, polyphenylsulfone, poly(vinyl chloride) (PVC), polyoxymethylene, polyacrylonitrile (PAN), polystyrene, poly(vinyl alcohol) (PVA), poly(DL-lactide) (PDLA), poly(L-lactide) (PLLA), poly(glycolide) (PGA), poly(ε-caprolactone) (PCL), poly (dioxanone) (PDO), poly(glyconate), poly(hydroxybutyrate) (PHB), poly(hydroxyvalerate (PHV), poly(orthoesters), poly(carboxylates), poly(propylene fumarate), poly(phosphates), poly(carbonates), poly(anhydrides), poly(iminocarbonates), poly(phosphazenes), polyimides, polyamides, polysiloxanes, polyphosphates, citric-acid based polymers, polyacrylics, polymethylmethacrylate (PMMA), bisphenol A-glycidyl methacrylate (bis-GMA), tri(ethylene glycol) dimethacrylate (TEG-DMA), poly(2-hydroxyethyl methacrylate) (HEMA), poly(acrylic acid) (PAA), polyethylene glycol (PEG), polysaccharides, gelatin, collagen, alginate, chitosan, dextran, carboxymethyl cellulose, polypeptides, copolymers thereof, and blends thereof.

The nanoparticles (101) defined herein have an average particle diameter or a size distribution in the range from about 1 nm to about 1000 nm. Depending on the application of the methacrylate-modified nanoparticles (also sometimes referred to herein as "MA NPs") the diameter is optionally in the range from about 1 to about 200 nm for in vivo targeting and drug delivery, optionally in the range from about 10 nm to about 150 nm for plasmonic properties, optionally in the range from about 1 nm to about 100 nm for imaging/detection probes. In some particular embodiments, the nanoparticle size may be in the range from about 1 nm to about 10 nm and may be in the range of from about 3 nm to about 6 nm to achieve renal clearance from the body of a subject after implantation or administration a material or reagent according to the disclosure.

In various embodiments, methacrylate-modified nanoparticles defined herein are not limited to nanoscale particles but also include microspheres, which have an average particle diameter or size distribution between 1 μm and 1000 μm, for example for delivery of bioactive agents and drugs.

As disclosed herein, nanoparticles are generally considered spherical in shape, but not limited to other shapes including, but not limited to nanopheres, nanorods, nanoplates, nanoshells, nanotubes, nanocages, and nanostars.

In some embodiments, the nanoparticles are composed of a combination of at least two materials including, but is not limited to, a metal, a ceramic (e.g., an oxide), a semiconductor, and a polymer, each material forming at least a portion of the nanoparticle, wherein the nanoparticles have a core-shell structure or a Janus structure.

Nanoparticle Properties

The nanoparticles within the photocrosslinkable agent may exhibit advantageous physical interactions with radiation (or photons) at wavelengths across the electromagnetic spectrum, as well as with electrons. These interactions—including absorption, emission, surface plasmon resonance, scattering, and transmission—may enable any number of functionalities for drug delivery, signal transduction, diagnostic imaging, and sensing.

The nanoparticles within the photocrosslinkable agent may enable non-invasive, imaging of a photocrosslinked material or structure, including longitudinal, quantitative imaging of degradation and/or drug delivery. The nanoparticle may provide imaging contrast using any suitable non-invasive imaging modality including, but not limited to, radiography, X-ray computed tomography (CT), photon-counting spectral CT, magnetic resonance imaging (MRI), magnetic resonance spectroscopy (MRS), ultrasound elasticity imaging, photoacoustic imaging, photothermal imaging, near-infrared fluorescence imaging, optical coherence tomography, positron emission tomography (PET), and single-photon emission computed tomography (SPECT), among others.

Molecules and Ligands

In accordance with the various embodiments, the methacrylate-modified nanoparticles are prepared using a variety of molecules or bifunctional molecules and comprise on their surfaces a plurality of molecules as described herein.

As more fully described herein below, attachment of the molecules to the surface of the nanoparticle includes one or more alternate reaction paths to attach surface ligands.

Figure 5:
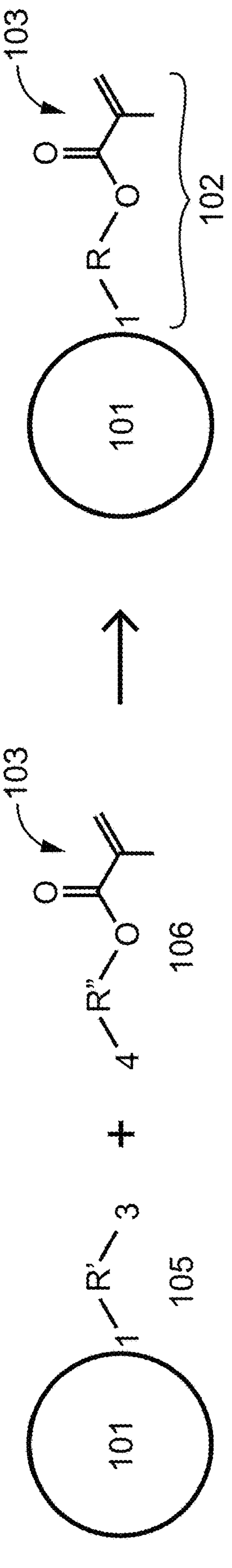
FIG. 5 shows a graphical representation of an embodiment of the method for creating the methacrylate-modified nanoparticle (100) shown in FIGS. 1 and 3.

Referring again to the drawings, FIG. 5 shows a method for creating the methacrylate-modified nanoparticle shown in FIGS. 1 and 3. A bifunctional molecule (105) is provided with a ligand (1) capable of attaching to the nanoparticle (101) surface opposite a reactive terminal ligand (3) capable of covalent linking to another molecule. A second bifunctional molecule (106) is provided with a terminal methacrylate ligand (103) opposite a coupling ligand (4) capable of covalent linking to reactive terminal ligand (3). As commonly used in the art, R, R' and R" denote any suitable molecular structure between the terminal ligands, and R is the result of covalently linking R' and R".

Figure 6:
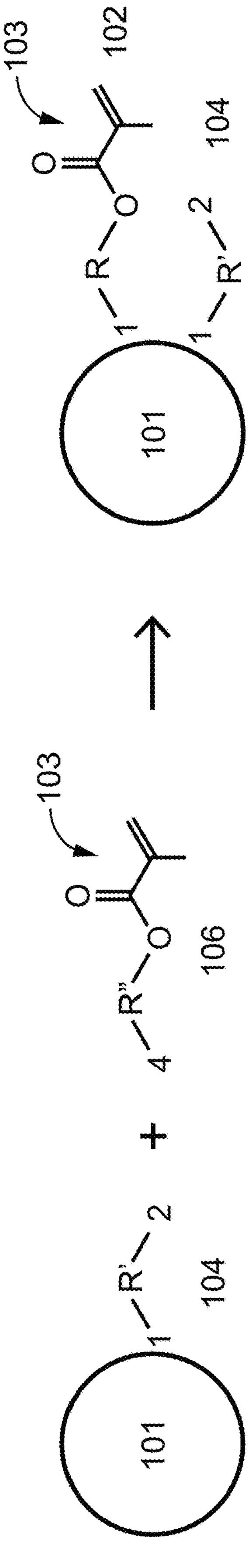
FIG. 6 shows a graphical representation of another embodiment of the method for creating the methacrylate-modified nanoparticle (100) shown in FIGS. 1 and 4.

Referring again to the drawings, FIG. 6 shows another embodiment of the method in FIG. 5 for creating the methacrylate-modified nanoparticle shown in FIGS. 1 and 4. A bifunctional molecule (104) is provided with a ligand (1) capable of attaching to the nanoparticle (101) surface opposite a hydrophilic terminal ligand (2) capable of covalent linking to another molecule. A second bifunctional molecule (106) is provided with a terminal methacrylate ligand (103) opposite a coupling ligand (4) capable of covalent linking to hydrophilic terminal ligand (2). The covalent linking reaction is carried out under conditions that result in incomplete conversion of the hydrophilic terminal ligands (2) such that the nanoparticle is surface functionalized with a methacrylate-terminated molecule and a second molecule with a hydrophilic terminal ligand. The relative amount of hydrophobic methacrylate-terminated molecules and molecules with a hydrophilic terminal ligand may be tailored to control the aqueous solubility of the surface modified nanoparticles. As commonly used in the art, R, R' and R" denote any suitable molecular structure between the terminal ligands, and R is the result of covalently linking R' and R".

Nanoparticle Surface Attachment Ligand (1)

In various embodiments, methacrylate-modified nanoparticles include molecules that are attached to the surface by at least one nanoparticle surface attachment ligand. In some embodiments, the nanoparticle surface attachment ligand (1) includes, but is not limited to, thiols, amines, alcohols, silanes, carboxylates, phosphonates, and combinations thereof.

In embodiments, wherein 101 is a metal nanoparticle, a suitable (1) may be a chemical with one or more terminal ligands being thiol, amine, or the combination thereof.

In embodiments, wherein 101 is ceramic nanoparticle or a metal nanoparticle with an oxidized surface, a suitable (1) may be a chemical with one or more terminal ligands being silane, carboxylate, phosphonate, amine, or the combination thereof.

In embodiments, wherein 101 is a semiconductor nanoparticle, a suitable (1) may be a chemical with one or more terminal ligands being thiol, silanes, amine, or the combination thereof.

In embodiments, wherein 101 is a polymer nanoparticle that has free amine, alcohol, carboxylate in the polymer backbone or a polymer can be modified with amine, alcohol, carboxylate functional groups on the polymer backbone. In this embodiment, a suitable (1) may be avoided because the nanoparticle presents ligands (2) or (3) without the addition of molecules (105) or (106), respectively.

It will be appreciated by one of ordinary skill in the art that the selection of the most appropriate ligand (1) will be governed by the nanoparticle surface composition.

Hydrophilic Terminal Ligand (2) and Reactive Terminal Ligand (3)

In various embodiments, methacrylate-modified nanoparticles include molecules that include terminal ligands that are positioned opposite the ligands that are attached to the surface. In some embodiments, the terminal ligand is a hydrophilic terminal ligand (2).

In some embodiments, the at least one hydrophilic terminal ligand (2) includes, but is not limited to, thiols, amines, alcohols, carboxylates, silanes, phosphonates, acrylates, epoxides, and combinations thereof.

In some embodiments, the methacrylate-modified nanoparticle has water solubility that is controlled by the relative amounts of the terminal methacrylate ligand (103) and the hydrophilic terminal ligand (2).

A hydrophilic terminal ligand (2) or reactive terminal ligand (3) is capable of covalent linking to another molecule 106, suitable (2) (or 3) can be selected from following list:

In embodiments, wherein (1) is a thiol, a suitable (2) includes, but is not limited to, an amine, alcohol, carboxylate, or silane.

In embodiments, wherein (1) is a silane, a suitable (2) includes, but is not limited to, an acrylate, amine, epoxy, or alcohol.

In embodiments, wherein (1) is an amine, a suitable (2) includes, but is not limited to, an amine.

In embodiments, wherein (1) is a carboxylate, a suitable (2) includes, but is not limited to, a carboxylate.

In embodiments, wherein (1) is a phosphonate, a suitable (2) includes, but is not limited to, an amine.

It will be appreciated by one of ordinary skill in the art that the selection of the most appropriate hydrophilic terminal ligand (2) will be influenced by the selection of ligand (1) and coupling reaction as described herein below.

Referring again to the drawings, in FIG. 5, the hydrophilic terminal ligand is represented as (2) and in FIG. 6, the reactive terminal ligand is represented as (3). It will be appreciated that in these drawings, each of the referenced ligands may be hydrophilic, though the specific active chemical group on each may be different. In other embodiments, each of the hydrophilic terminal ligand (2) and reactive terminal ligand (3) may be different. Thus, in a possible embodiment for each of FIG. 5 and FIG. 6, the hydrophilic terminal ligand (2) and the reactive terminal ligand (3) may comprise the same terminal chemical group, for example a carboxylate chemical group. In other possible embodiments, each of the hydrophilic terminal ligand (2) and the hydrophilic reactive ligand (3), respectively, may comprise different groups.

Coupling Ligand

A coupling ligand (4) is capable of covalent linking to hydrophilic terminal ligand (2) or reactive terminal ligand (3). Suitable coupling ligands (4) can be selected from following list:

In embodiments, wherein (2) or (3) is an acrylate, coupling ligand (4) can be avoided.

In embodiments, wherein (2) or (3) is an amine, a suitable coupling ligand (4) includes, but is not limited to, a carboxylate or epoxy.

In embodiments, wherein (2) or (3) is an alcohol, a suitable coupling ligand (4) includes, but is not limited to, a carboxylate, silane, or epoxy.

In embodiments, wherein (2) or (3) is a carboxylic acid, a suitable coupling ligand (4) includes, but is not limited to, an amine or alcohol.

In embodiments, wherein (2) or (3) is a silane, a suitable coupling ligand (4) includes, but is not limited to, an alcohol.

In embodiments, wherein (2) or (3) is an epoxy, a suitable coupling ligand (4) includes, but is not limited to, an amine, alcohol, or thiol.

Method for Preparing Methacrylate-Modified Nanoparticles

In accordance with various embodiments, the disclosure also provides a method for providing a photocrosslinkable agent, the method comprising providing a nanoparticle, providing a first bifunctional molecule (105) comprising at least one nanoparticle surface attachment ligand (1) that is attached to a surface of the nanoparticle, and at least one terminal ligand comprising a hydrophilic terminal ligand (2) capable of covalent linking to a terminal ligand of another molecule, providing a second bifunctional molecule (106)

comprising at least one terminal methacrylate ligand (103) and at least one terminal ligand comprising a coupling ligand (4) capable of covalent linking to the hydrophilic terminal ligand (2) of the first molecule, and covalently linking the hydrophilic terminal ligand (2) of the first molecule to the coupling ligand (4) of the second molecule, optionally in the presence of a coupling agent or catalyst.

In some embodiments, the hydrophilic terminal ligand (2) of the first molecule is hydrophilic, and wherein covalent linking to the coupling ligand (4) of the second molecule is carried out under conditions that result in incomplete conversion of the hydrophilic terminal coupling ligands (2) such that the nanoparticle is surface functionalized with a conjugated molecule comprising a nanoparticle surface attachment ligand (1) and a terminal methacrylate ligand (103), and the first molecule comprising the nanoparticle surface attachment ligand (1) and the hydrophilic terminal ligand (2), and wherein the methacrylate-modified nanoparticle has a water solubility that is controlled by the relative amounts of the conjugated molecule and the first molecule.

Coupling Reaction Chemistry

In various embodiments, the disclosure provides at least five types of reaction chemistry that can be used to link hydrophilic terminal ligand (2) (or 3) with a coupling ligand (4), depending on the type of (2) (or 3) and coupling ligand (4) used in specific embodiments. A suitable coupling agent may be needed for each of the reaction chemistries to link hydrophilic terminal ligand (2) or (3) with (4). Suitable coupling agents are provided below for each reaction chemistry and selected ligand pairs.

Type 1. "EDC/NHS chemistry" Carboxyl-to-amine reaction chemistry, wherein EDC, EDC/NHS, DCC, or DCC/NHS can be used as a suitable coupling agent.

Coupling agents: In embodiments, wherein carboxyl-to-amine reaction chemistry is followed for coupling reaction, wherein hydrophilic terminal ligand (2) and coupling ligand (4) is a pair of amine and carboxylate, a suitable coupling agent may be a 1-ethyl-3-(3-dimethylaminopropyl) carbodiimide hydrochloride (EDC) or dicyclohexyl carbodiimide (DCC) alone, or the combination of EDC and N-hydroxysuccinimide (NHS), or a combination of DCC and NHS. N-hydroxysulfosuccinimide (sulfoNHS) may optionally be used in place of NHS.

Type 2. "Steglich esterification chemistry" Carboxyl-to-hydroxyl_Steglich esterification chemistry, wherein DCC can serve as a suitable coupling agent.

Coupling agents: In embodiments, wherein Steglich esterification chemistry is followed for coupling reaction, wherein hydrophilic terminal ligand (2) and coupling ligand (4) is a pair of alcohol and carboxylate, a suitable coupling agent may be a combination of DCC and 4-dimethylaminopyridine.

Type 3. "Silane-hydroxyl coupling chemistry" wherein a silane itself can serve as a suitable coupling agent so that no additional coupling agent is needed.

Coupling Agents: In some embodiments, wherein silane-hydroxyl coupling chemistry is followed for coupling reaction, wherein hydrophilic terminal ligand (2) and coupling ligand (4) is a pair of hydroxyl and silane, no additional coupling agent is needed. In this case, silane is the coupling agent. In a particular embodiment, wherein (1) is silane and (2) (or 3) are acrylate but coupling ligand (4) is avoided, no coupling agent is needed.

Type 4. "Epoxide ring opening chemistry", including epoxy-thiol ring opening, epoxy-amine ring opening, and epoxy-alcohol ring opening, wherein no additional coupling agent is needed.

Coupling Agents: In embodiments, wherein epoxide ring opening chemistry is followed for coupling reaction, wherein hydrophilic terminal ligand (2) and coupling ligand (4) is a pair of amine and epoxy, or a pair of alcohol and epoxy, no coupling agent is needed.

Type 5. "Maleimide reaction chemistry," wherein hydrophilic terminal ligand (2) and coupling ligand (4) is a pair of maleimide and thiol, or a pair of maleimide and amine, wherein no additional coupling agent is needed.

Preparation of Molecules (Including NP Attached and Reactive Molecules for Forming the MA-NPs To synthesize a MA-NPs, the bifunctional molecule (104, 105, 106, 102) can be selected from following list, which is classified based on the linking reaction chemistry between 104/105 and 106.

Carboxyl-to-Amine Reaction Chemistry

In embodiments, wherein carboxyl-to-amine reaction chemistry is followed for coupling reaction, wherein the hydrophilic terminal ligand (2) and coupling ligand (4) are amine and carboxylate, (104) (or 105) may include, but is not limited to, a mercapto amine polymer with free amine on the backbone, bifunctional amine, amino phosphonic acid, or amino silane. Accordingly, (106) may include, but is not limited to, an acrylic acid or acyl chloride.

In embodiments, wherein carboxyl-to-amine reaction chemistry is followed for coupling reaction, wherein the hydrophilic terminal ligand (2) and coupling ligand (4) are carboxylate and amine, (104) (or 105) may include, but is not limited to, a mercapto acid, polymer with free carboxylate on the backbone, or bifunctional carboxylic acid. Accordingly, (106) may include, but is not limited to, an amino acrylate.

Carboxyl-to-Hydroxyl Steglich Esterification Chemistry

In embodiments, wherein carboxyl-to-hydroxyl Steglich esterification is followed for coupling reaction, wherein the hydrophilic terminal ligand (2) and coupling ligand (4) are carboxylate and hydroxyl, (104) (or 105) may include, but is not limited to, a mercapto acid, polymer with free carboxylate on the backbone, or bifunctional carboxylic acid. Accordingly, (106) may include, but is not limited to, a hydroxyl acrylate.

In embodiments, wherein carboxyl-to-hydroxyl Steglich esterification is followed for coupling reaction, wherein the hydrophilic terminal ligand (2) and coupling ligand (4) are hydroxyl and carboxylate, (104) (or 105) may include, but is not limited to, a mercapto alcohol, or polymer with free hydroxyl on the backbone. Accordingly, (106) may include, but is not limited to, an acrylic acid or acyl chloride.

Silane-Hydroxyl Coupling Chemistry

In embodiments, wherein silane-hydroxyl coupling is followed for coupling reaction, wherein the hydrophilic terminal ligand (2) and coupling ligand (4) are hydroxyl and silane, (104) (or 105) may include, but is not limited to, a mercapto alcohol, or polymer with free hydroxyl on the backbone. Accordingly, (106) may include, but is not limited to, acrylate silanes.

In embodiments, wherein silane-hydroxyl coupling is followed for coupling reaction, wherein the hydrophilic terminal ligand (2) and coupling ligand (4) are silane and hydroxyl, (104) (or 105) may include, but is not limited to, an acrylate silane. Accordingly, (106) can be avoided. In this case, a bifunctional molecule (105) is equal to (102).

Epoxide Ring Opening Chemistry

In embodiments, wherein epoxide ring opening is followed for coupling reaction, wherein the hydrophilic terminal ligand (2) and coupling ligand (4) are epoxy and hydroxyl, (104) (or 105) may include, but is not limited to, an epoxy silane. Accordingly, (106) may include, but is not limited to, an amino acrylate, or hydroxyl acrylate.

In embodiments, wherein epoxide ring opening is followed for coupling reaction, wherein the hydrophilic terminal ligand (2) and coupling ligand (4) are amine and epoxy, (104) (or 105) may include, but is not limited to, a mercapto amine, polymer with free amine on the backbone, bifunctional amine, amino phosphonic acid, or amino silane. Accordingly, (106) may include, but is not limited to, an acrylic epoxy.

Maleimide Reaction Chemistry

In embodiments, wherein maleimide reaction chemistry is followed for coupling reaction, wherein the hydrophilic terminal ligand (2) and coupling ligand (4) are maleimide and thiol, (104) (or 105) may include, but is not limited to, a thiol-maleimide, silane-maleimide, or amino maleimide. Accordingly, (106) may include, but is not limited to, an amino acrylate, or hydroxyl acrylate.

In embodiments, wherein maleimide reaction chemistry is followed for coupling reaction, wherein the hydrophilic terminal ligand (2) and coupling ligand (4) maleimide and amine, (104) (or 105) may include, but is not limited to, a thiol-maleimide, silane-maleimide, or amino maleimide. Accordingly, (106) may include, but is not limited to, an amino acrylate.

Materials Formed and Compared to Prior Art

Materials, including polymer networks or hydrogels, that are formed according to the disclosure have been evaluated and the results are described further herein below and in the Examples that follow. In general, the methods and resultant formed materials may be depicted graphically to illustrate visually the nature of interaction among the MA-NPs and a polymer network.

Figure 7:
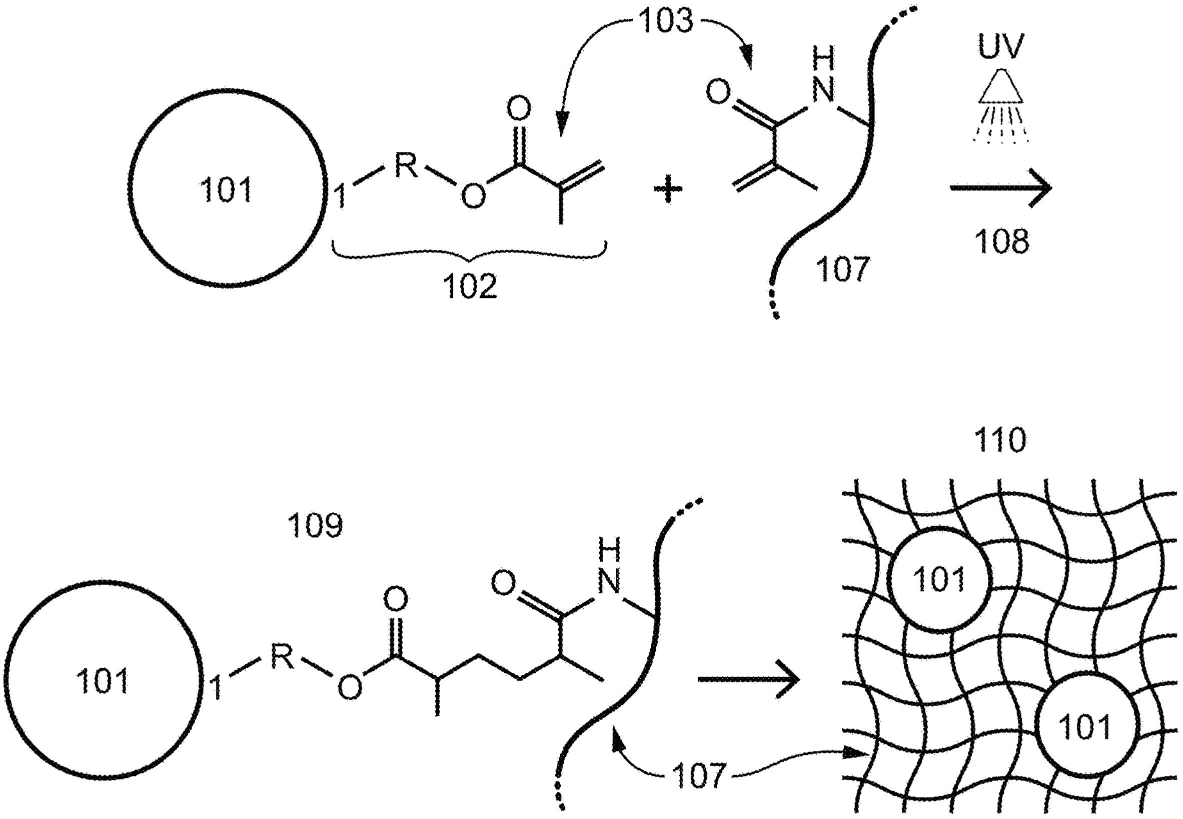
FIG. 7 shows a graphical representation an embodiment of the invention where a methacrylate-modified nanoparticle, such as that shown in FIGS. 3 and 4 and prepared in FIGS. 5 and 6, is photocrosslinked to methacrylate-modified macromolecules (107) in the presence of a suitable photoinitiator (108) resulting in a covalent linkage (109) between the nanoparticle and macromolecule.

Referring again to the drawings, FIG. 7 shows an embodiment of the invention where a methacrylate-modified nanoparticle, such as that shown in FIGS. 3 and 4 and prepared in FIGS. 5 and 6, is able to be photocrosslinked to methacrylate-modified macromolecules (107) in the presence of a suitable photoinitiator (108) resulting in a covalent linkage between the nanoparticle and macromolecule (109). Thus, a photocrosslinked hydrogel or polymer with covalently-linked nanoparticles (110) is prepared in one-step with minimal disruption to the molecular network or crosslinking density.

FIG. 7 depicts graphically what has been demonstrated in the Examples. In particular, the formed material, in the exemplified instance, a hydrogel, demonstrates favorable features and is formed by a simple, one step method. This is in contrast to what has been shown in the prior art.

Figure 8:
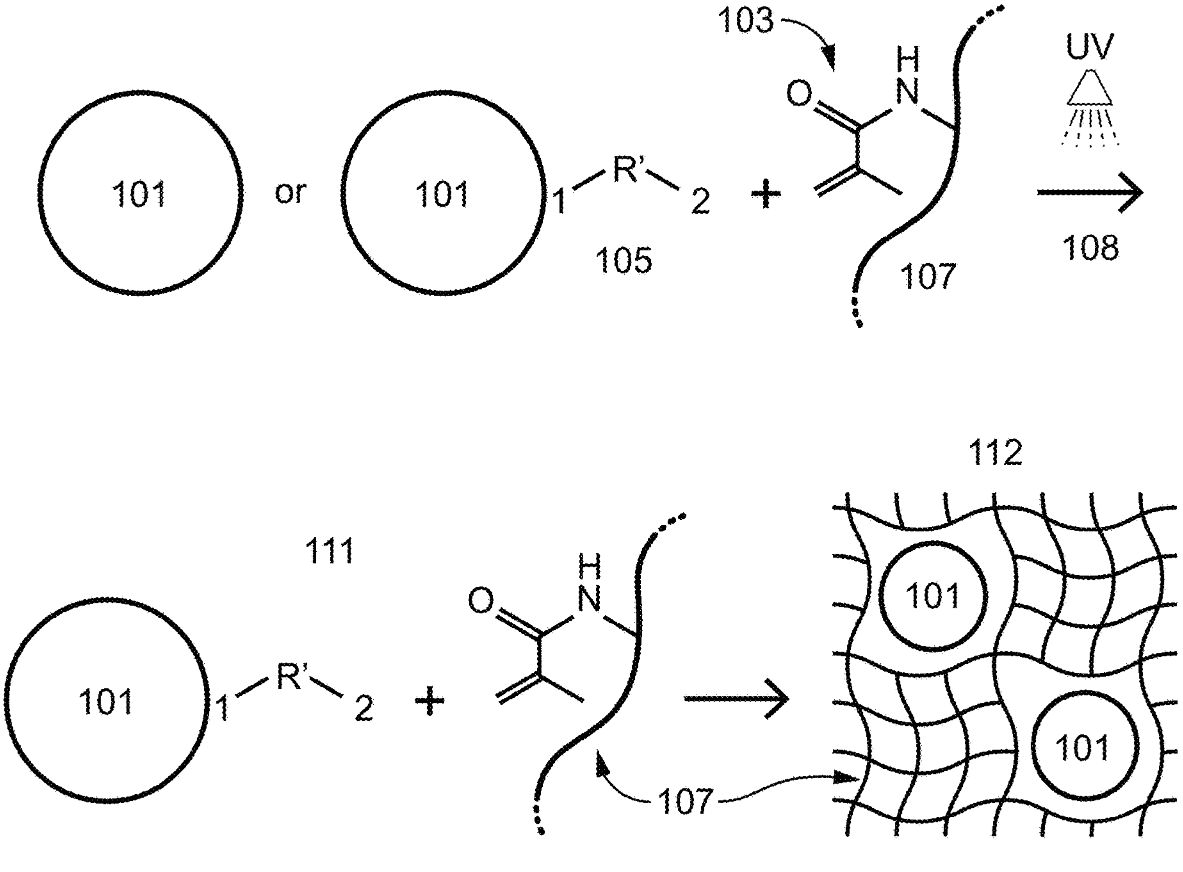
FIG. 8 shows a graphical representation of a prior art method as compared to FIG. 7.

Referring again to the drawings, FIG. 8 shows an example of the prior art for comparison to FIG. 7, where nanoparticles (101) with either bare surfaces or surface functionalized with molecules having a hydrophilic terminal ligand (105) are physically mixed with methacrylate-modified macromolecules (107). The methacrylate-modified macromolecules (107) are photocrosslinked in the presence of a suitable photoinitiator (108) but nanoparticles are unable to form covalent linkages with the methacrylate-modified macromolecules (111). Thus, a photocrosslinked hydrogel or polymer with encapsulated nanoparticles (112) is prepared in one-step with disruption to the molecular network or crosslinking density.

Figure 9:
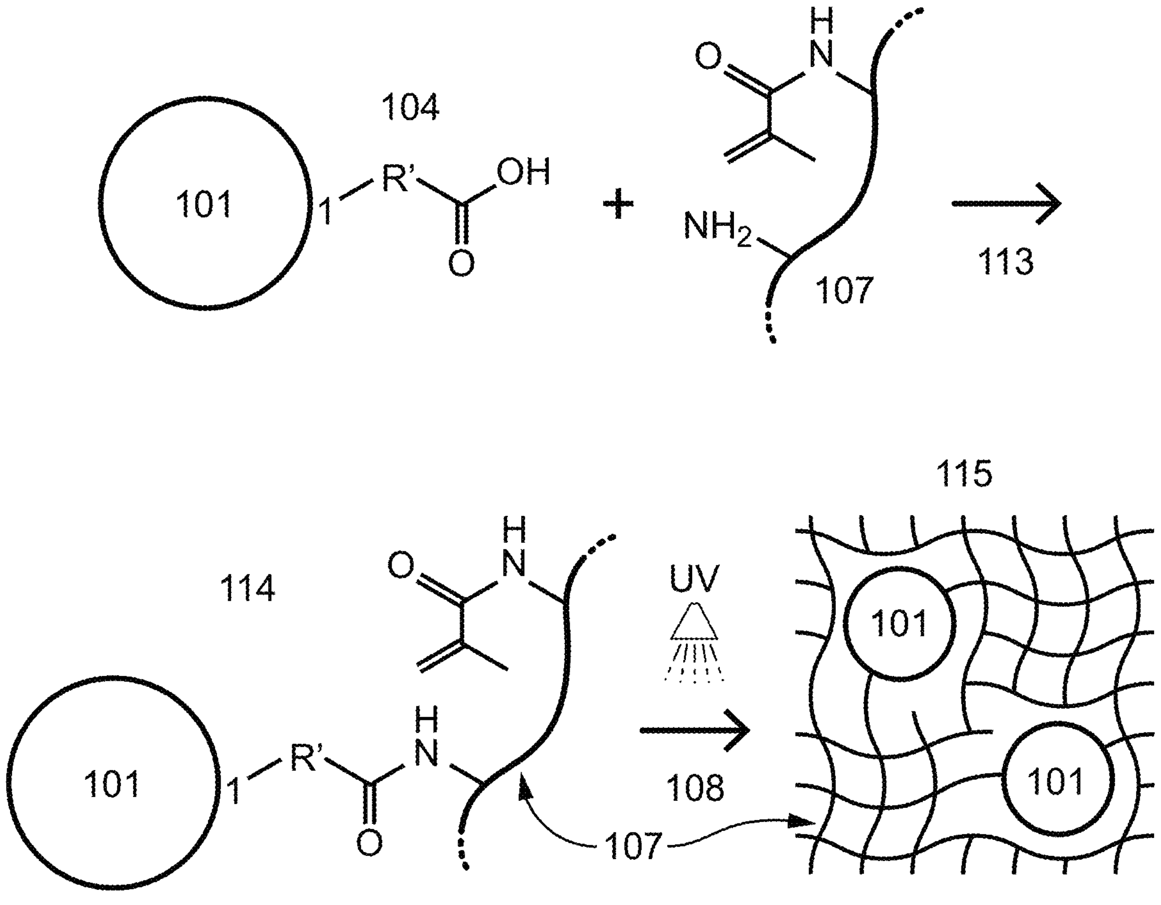
FIG. 9 shows another graphical representation of a prior art method as compared to FIG. 7.

Referring again to the drawings, FIG. 9 shows an example of the prior art for comparison to FIG. 7, where a surface-modified nanoparticle (104) is covalently-linked (114) to methacrylate-modified macromolecules (107) before photocrosslinking the methacrylate-modified macromolecules in the presence of a suitable photoinitiator (108). Thus, a photocrosslinked hydrogel or polymer with covalently-linked nanoparticles (110) is prepared in two-steps with disruption to the molecular network or crosslinking density. Covalent-linking of surface modified nanoparticles to methacrylate-modified macromolecules may utilize any suitable means, such as EDC/NHS chemistry with carboxylate and amine ligands, as shown.

Photocrosslinkable Ink and Photocrosslinked Material/Hydrogel Formed Therewith

In accordance with various embodiments, the disclosure also provides a photocrosslinkable ink for forming a material or structure, comprising: a suitable solvent at least one of a plurality of methacrylate-modified nanoparticles, the at least one of a plurality of methacrylate-modified nanoparticles comprising a nanoparticle; a plurality of molecules attached to the surface of the nanoparticle, at least a portion of the plurality of molecules comprising at least a first molecule comprising at least one nanoparticle surface attachment ligand (1) and at least one terminal methacrylate ligand (103); optionally a plurality of methacrylate-modified macromolecules (107); and a photoinitiator.

In some embodiments, the plurality of methacrylate-modified macromolecules (107) includes, but is not limited to, polymers, oligomers or a combination thereof which including, but not limited to, gelatin-methacrylate (gelMA), collagen-methacrylate (colMA), alginate-methacrylate (algMA), hyaluronic acid-methacrylate (HAMA), dextran-methacrylate (dexMA), chitosan-methacrylate (chiMA), chondroitin sulfate-methacrylate (CSMA), heparin-methacrylate (hepMA), carboxymethyl cellulose-methacrylate (CMCMA), polyethylene glycol dimethacrylate (PEGDA), polyurethane-methacrylate, polyacrylic acid (PAA), polymethyl methacrylate (PMMA), poly(2-hydroxyethyl methacrylate) (HEMA), bisphenol A-glycidyl methacrylate (bis-GMA), tri(ethylene glycol) dimethacrylate (TEG-DMA), diethyleneglycol diacrylate (DEGDA), and combinations thereof.

In some embodiments, the solvent is water, the at least one of a plurality of methacrylate-modified nanoparticles further comprising at least a second molecule, the second molecule comprising at least one nanoparticle surface attachment ligand (1) and at least one hydrophilic terminal ligand (2).

In some embodiments, the at least one of a plurality of methacrylate-modified nanoparticles has water solubility that is controlled by the relative amounts of the terminal methacrylate ligand (103) and the hydrophilic terminal ligand (2).

In some embodiments, the photocrosslinkable ink comprises a plurality of methacrylate-modified nanoparticles, wherein at least a portion of the plurality of methacrylate-modified nanoparticles are photocrosslinked with at least a portion of the plurality of methacrylate-modified macromolecules (107), resulting in a covalent linkage between at least a portion of the nanoparticles and methacrylate-modified macromolecules (107), prior to photocrosslinking all the methacrylate-modified nanoparticles and methacrylate-modified macromolecules (107).

In some embodiments, the solvent is water and the photocrosslinkable ink further comprises cells and/or biomolecules, the biomolecules including but not limited to proteins, carbohydrates, lipids, peptides, proteases, and nucleic acids.

In accordance with various embodiments, the disclosure also provides a photocrosslinked material comprising the photocrosslinkable agent.

In some embodiments, the photocrosslinked material comprises at least one of a plurality of methacrylate-modified nanoparticles, wherein at least one of a plurality of methacrylate-modified nanoparticles of the photocrosslinkable agent is photocrosslinked within a plurality of methacrylate-modified macromolecules (107), wherein at least a portion of the plurality of the terminal methacrylate ligands (103) are photocrosslinked with at least a portion of the methacrylate-modified macromolecules (107), the photocrosslinked material comprising a covalent linkage between the photocrosslinked methacrylate-modified nanoparticles and methacrylate-modified macromolecules (107).

In some embodiments, the photocrosslinked material exhibits at least one or more properties that includes, but is not limited to crosslinking density, rheology, mechanical stiffness, mechanical strength, swelling, degradation kinetics, and any combination thereof, and wherein at least one or more of the properties are not substantially altered by the presence of the photocrosslinkable agent as compared to a photocrosslinked product formed by photocrosslinking the methacrylate-modified macromolecules (107) in the absence of the photocrosslinkable agent.

In accordance with various embodiments, the disclosure also provides a photocrosslinked material comprising the photocrosslinkable agent wherein the photocrosslinkable agent is photocrosslinked. In some embodiments, at least a portion of the plurality of the terminal methacrylate ligands (103) are photocrosslinked, resulting in a covalent linkage between photocrosslinked methacrylate-modified nanoparticles (107).

In accordance with various embodiments, the disclosure also provides a method of forming a photocrosslinked material comprising, providing the photocrosslinkable ink and photocrosslinking the provided photocrosslinkable ink.

In some embodiments, the plurality of methacrylate-modified macromolecules (107) includes, but is not limited to, polymers, oligomers or a combination thereof including, but is not limited to, gelatin-methacrylate (gelMA), collagen-methacrylate (colMA), alginate-methacrylate (algMA), hyaluronic acid-methacrylate (HAMA), dextran-methacrylate (dexMA), chitosan-methacrylate (chiMA), chondroitin sulfate-methacrylate (CSMA), heparin-methacrylate (hepMA), carboxymethyl cellulose-methacrylate (CMCMA), polyethylene glycol dimethacrylate (PEGDA), polyurethane-methacrylate, polyacrylic acid (PAA), polymethyl methacrylate (PMMA), poly(2-hydroxyethyl methacrylate) (HEMA), bisphenol A-glycidyl methacrylate (bis-GMA), tri(ethylene glycol) dimethacrylate (TEG-DMA), diethyleneglycol diacrylate (DEGDA), and combinations thereof.

In some embodiments, the solvent is water, the methacrylate-modified nanoparticles further comprising at least a second molecule, the second molecule comprising at least one nanoparticle surface attachment ligand (1) and at least one hydrophilic terminal ligand (2).

In some embodiments, the methacrylate-modified nanoparticle has water solubility that is controlled by the relative amounts of the terminal methacrylate ligand (103) and the hydrophilic terminal ligand (2).

Methacrylate-Modified Macromolecules

In various embodiments for forming networks using a methacrylate-modified macromolecule (107), the methacrylate-modified macromolecule (107) may be include, but is not limited to polymers, oligomers or a combination thereof including, but not limited to, gelatin-methacrylate (gelMA), collagen-methacrylate (colMA), alginate-methacrylate (algMA), hyaluronic acid-methacrylate (HAMA), dextran-methacrylate (dexMA), chitosan-methacrylate (chiMA), chondroitin sulfate-methacrylate (CSMA), heparin-methacrylate (hepMA), carboxymethyl cellulose-methacrylate (CMCMA), polyethylene glycol diacrylate (PEGDA), polyurethane-methacrylate, polyacrylic acid (PAA), polymethyl methacrylate (PMMA), poly(2-hydroxyethyl methacrylate) (HEMA), bisphenol A-glycidyl methacrylate (bis-GMA), tri(ethylene glycol) dimethacrylate (TEG-DMA), diethyleneglycol diacrylate (DEGDA), and combinations thereof.

The degree of methacryloyl substitution directly influences 1) the cross-linking density of the hydrogel matrix, and 2) the available sites for MA-NPs to be conjugated, which is preferably greater than 10%. For example, in some embodiment, the degree of methacryloyl substitution is preferably greater than 40% for gelMA, preferably greater than 20% for HAMA, preferably greater than 20% for ColMA.

The molecular weight (Mw) is another important factor that influences the crosslinking density, mechanical, viscoelastic and degradation properties, which is preferably greater than 2 kDa, preferably greater than 20 kDa for gelMA, preferably greater than 20% for HAMA, preferably greater than 20% for ColMA.

The invention provides a bioink composition comprising MA-NPs, methacrylate-modified macromolecules (MA-macromolecules), and a photoinitiator, and a method for the preparation.

Photoinitiator

In various embodiments, inks and other compositions herein may include a photoinitiator. A photoinitiator is a molecule that creates reactive species when exposed to radiation (UV or visible), and then induces the photocrosslinking of MA-macromolecules.

In some embodiments, a photoinitiator in this invention can be selected from a wide range, including but not limit to 2-Hydroxy-4-(2-hydroxyethoxy)-2-methylpropiophenone (Irgacure 2959), lithium phenyl-2,4,6-trimethylbenzoylphosphinate (LAP), camphorquinone, thioxanthone and benzophenone, and visible light-sensitive photoinitiator, eosin Y, and combinations thereof. Thus, a photoinitiator may be include, but is not limited to, 2-Hydroxy-4-(2-hydroxyethoxy)-2-methylpropiophenone (Irgacure 2959), LAP, camphorquinone, thioxanthone and benzophenone, and visible light-sensitive photoinitiator, eosin Y, and combinations thereof.

Composition Content

In various embodiments, the MA-NP concentration in inks and other compositions described herein may be varied depending on designed applications. For example, in some particular embodiments, the MA-NP concentration is preferably greater than 5 mM for in vitro micro-CT imaging. In some particular embodiments, the MA-NP concentration is preferably greater than 0.5 wt % (w/v) based on the total volume of the bioink composition for reinforcement.

In some embodiments, the MA-macromolecule content in inks and other compositions described herein may be greater than 0.1% (w/v) based on the total volume of the bioink composition. In the embodiment in the first example, the content is in the range from about 2% to about 40% for gelMA. In the embodiment in the second example, the content is in the range from about 0.5% to about 10% for HAMA. In some embodiments, the content is in the range from about 0.3% to about 0.8% for ColMA.

The photoinitiator concentration in inks and other compositions described herein may be varied in the range from about 0.01% to about 2.0% (w/v) depending on the solubility of photoinitiator, designed polymerization rate, functionality, and application. In some embodiments, the concentration is in the range from about 0.05% to about 1.5% (w/v) for a bioink. In some embodiments, cells or biomolecules may be added to the bioink.

In some embodiments, the nanoparticle concentration is in the range of from about 0.1 to about 200 mM based on the total ink volume.

In some embodiments, the nanoparticle concentration is in the range of from about 1 nM to about 100 mM for imaging and drug delivery. In some embodiments, the nanoparticle concentration is in the range of from about 1 μM to about 10 mM. In some embodiments, the nanoparticle concentration is in the range of from about 1 to about 100 mM for radiographic imaging.

In various embodiments the nanoparticle concentration is in the range from about 1% to about 99% by volume of the ink volume for mechanical reinforcement or bioactive filler. In some embodiments, the nanoparticle concentration is in the range of from about 1% to about 50%, or from about 1% to about 20%, or from about 1% to about 10%.

In some embodiments, the methacrylate-modified macromolecule concentration is in the range of about 0.1% to about 40% (w/v) based on the total ink volume.

In some embodiments, the methacrylate-modified macromolecule concentration is in the range of about 0.1% to about 1% (w/v), or from about 0.5% to about 10%, or from about 2% to about 40%, depending on the MA-molecule used.

In some embodiments, the photoinitiator concentration is in the range from about 0.01% to about 2.0% (w/v) of the total ink volume.

In some embodiments, the photoinitiator concentration is in the range from about 0.05% to about 1.5% (w/v) for a bioink. In some embodiments, cells or biomolecules may be added to the bioink.

In some embodiments, the photocrosslinkable agent, MA-molecules and photoinitiator are incubated for 0.5 h to 7 days, or for 1-24 h before photocrosslinking.

EXAMPLES

Example 1: Methacrylate Gold Nanoparticles (AuMA NPs)

In one embodiment, AuMA NPs are synthesized by covalently-linking AuCOOH NPs with 2-aminoethyl methacrylate (AEMA) using EDC/NHS chemistry. Au NPs are first attached with mercaptosuccinic acid (MSA) to prepare hydrophilic AuCOOH NPs. AuCOOH NPs are then covalently linked with AEMA by EDC/NHS coupling. The coupling reaction is vigorously stirred under nitrogen protection at room temperature for a period time to obtain methacrylate-modified AuMA NPs. After the reaction, AuMA NPs are collected by centrifugation at 8400 g for 30 min and washed thrice with DI water.

In this embodiment, the molar feeding ratio of Au:EDC:NHS:AEMA influences the methcrylation degree and hydrophilicity of Au NPs, which may vary from 100:15:6:6 to 1:50:20:20. Higher proportion of EDC:NHS:AEMA is not recommend for preparing aqueous-soluble AuMA NPs due to the high degree of methacrylation.

The total time for coupling reaction also influences the methacrylation degree and hydrophilicity of Au NPs, which may vary from 3 to 48 h, preferably 24 h.

The pH condition of the reaction system influences the efficiency of coupling reaction, which is preferably between 4.0-8.5, more preferably between 6.0-7.5.

It may be appreciated that according to the disclosure, the molar feeding ratio of Au:EDC:NHS:MA influences the methacrylation degree and hydrophilicity of Au NPs, which may vary from 100:15:6:6 to 1:50:20:20. Higher proportion of EDC:NHS:MA is not recommend for preparing water-soluble AuMA NPs due to the high degree of methacrylation.

Example 2: Methacrylate-Modified 12 nm Gold Nanoparticles (AuMA NPs)

AuCOOH NPs were synthesized by surface functionalizing bare Au NPs, ~12 nm in diameter prepared by the citrate reduction method, with mercaptosuccinic acid (MSA). Briefly, 0.1 g gold (III) chloride trihydrate was added to 500 mL deionized (DI) water and heated to boiling while stirring. Once boiling, 0.5 g trisodium citrate dihydrate was added to the mixture. The mixture was boiled for another 20 min, cooled to room temperature, and stirred overnight. As-prepared Au NPs were collected in a volumetric flask and titrated to 500 mL. An aqueous solution containing 15 mL of 10 mM MSA was added to the Au NP solution and stirred overnight. As-prepared AuCOOH NPs were collected by centrifugation at ~11,000 g for 1 h and thrice washed with DI water.

AuMA NPs were synthesized by covalently-linking AuCOOH NPs with 2-aminoethyl methacrylate (AEMA) using EDC/NHS chemistry. First, 0.5 mmol AuCOOH NPs were added to 200 mL ethanol (80% v/v) containing 1.44 g 1-ethyl-3-(3-dimethylaminopropyl) carbodiimide hydrochloride (EDC) and 0.65 g N-hydroxysulfosuccinimide (NHS), which was then mixed with another 200 mL ethanol (80% v/v) containing 0.495 g fully dissolved AEMA, such that the molar ratio of Au:EDC:NHS:AEMA was 1:15:6:6. The mixture was vigorously stirred under nitrogen protection for 24 h at room temperature to obtain AuMA NPs. After the reaction, AuMA NPs were collected by centrifugation at 8400 g for 30 min and washed thrice with DI water.

Example 3: Methacrylate-Modified 5 nm Gold Nanoparticles (AuMA NPs)

AuCOOH NPs were synthesized by surface functionalizing bare Au NPs, ~5 nm in diameter prepared by a modified tannic acid/citrate reduction method, with mercaptosuccinic acid (MSA). Briefly, 93 mg gold (III) chloride trihydrate was added to 640 mL deionized (DI) water under stirring. A reducing solution was prepared by mixing 32 mL of 1 wt % sodium citrate, 32 mL of 1 wt % tannic acid, and 16 mL of 25 mM $K_2CO_3$ and 96 ml of DI. The $HAuCl_4$ and reducing solutions were both heated to 60° C. before adding the reducing solution to the $HAuCl_4$ solution and heating the combined solution to a boil. After 10 min of vigorous boiling, 53.6 mL of 30 wt % $H_2O_2$ was added, and the solution was boiled for an additional 10 min before removing heat and stirring the colloidal gold dispersion overnight. As-prepared AuCOOH NPs were collected by centrifugation in centrifugal filter unit (10 KDa NMWL) at 4000 g for 20 min and washed thrice with DI water.

AuMA NPs were synthesized by covalently-linking AuCOOH NPs with 2-aminoethyl methacrylate (AEMA) using EDC/NHS chemistry. First, 0.05 mmol AuCOOH NPs were added to 10 mL ethanol (80% v/v) containing 2.8 mg 1-ethyl-3-(3-dimethylaminopropyl) carbodiimide hydrochloride (EDC) and 1.3 mg N-hydroxysulfosuccinimide (NHS), which was then mixed with another 0.08 mL Dimethylformamide (DMF, 1.25% v/v) containing 1.1 mg fully dissolved AEMA, such that the molar ratio of Au:EDC:NHS:AEMA was 50:15:6:6. The mixture was vigorously stirred under nitrogen protection for 24 h at room temperature to obtain AuMA NPs. After the reaction, AuMA NPs were collected by centrifugation in centrifugal filter unit (10 KDa NMWL) at 4000 g for 20 min and washed thrice with DI water.

Example 4: Methacrylamide-Modified 12 nm Gold Nanoparticles (AuMA NPs)

AuCOOH NPs were synthesized by surface functionalizing bare Au NPs, ~12 nm in diameter prepared by the citrate reduction method, with mercaptosuccinic acid (MSA). Briefly, 0.1 g gold (III) chloride trihydrate was added to 500 mL deionized (DI) water and heated to boiling while stirring. Once boiling, 0.5 g trisodium citrate dihydrate was added to the mixture. The mixture was boiled for another 20 min, cooled to room temperature, and stirred overnight. As-prepared Au NPs were collected in a volumetric flask and titrated to 500 mL. An aqueous solution containing 15 mL of 10 mM MSA was added to the Au NP solution and stirred overnight. As-prepared AuCOOH NPs were collected by centrifugation at ~11,000 g for 1 h and thrice washed with DI water.

AuMA NPs were synthesized by covalently-linking AuCOOH NPs with 2-aminoethylmethacrylamide hydrochloride (AEMD, 98%) using EDC/NHS chemistry. First, 0.016 mmol AuCOOH NPs were added to 5.0 mL ethanol (80% v/v) containing 45.0 mg 1-ethyl-3-(3-dimethylaminopropyl) carbodiimide hydrochloride (EDC) and 21.0 mg N-hydroxysulfosuccinimide (NHS), which was then mixed with another 0.5 mL DI water containing 15.3 mg fully dissolved AEMD, such that the molar ratio of Au:EDC:NHS:AEMD was 1:15:6:6. The mixture was vigorously stirred under nitrogen protection for 24 h at room temperature to obtain AuMA NPs. After the reaction, AuMA NPs were collected by centrifugation at 8400 g for 30 min and washed thrice with DI water.

Example 5: Vinyl-Modified 2 nm Gold Nanoparticles

Au—C═C NPs were synthesized by surface functionalizing bare Au NPs, 2-3 nm in diameter prepared by the Brust method, with allyl mercaptan.

Briefly, an aqueous gold solution was prepared by dissolving 0.11 g gold (III) chloride trihydrate in 7.5 mL deionized (DI) water while stirring. An organic solution was prepared by dissolving 0.31 g tetra-n-octylammonium bromide in 25 ml of toluene. Then the aqueous gold solution was mixed with the organic solution and vigorously stirred until all the gold (III) was transferred into the organic layer. Once the yellow aqueous solution immediately became clear and the organic solution turned brown, the organic phase was transferred into a 50 mL flask and 0.03 g allyl mercaptan was added to the organic phase. Another aqueous solution was prepared by dissolving of 0.02 g sodium borohydride in 5.0 ml DI and then slowly added to the organic phase with vigorous stirring. After further stirring for 3 h, the organic phase was separated, evaporated in a rotary evaporator. The dark residue was suspended in 200 mL ethanol to remove excess thiol and kept overnight at −18° C. to precipitate. The dark brown precipitate was collected by filtration and washed twice with ethanol. The final product was dissolved in 2 ml toluene (or dried into powder).

Example 6: Preparation of a Photopolymerizable Ink

In various embodiments, the disclosure provides methods for preparing a reagent, such as an ink or a bioink, wherein the latter is particularly useful for biological and biomedical applications. In a first embodiment, the invention provides a method for producing a hydrogel composition, the method comprising the steps of.

Dissolve the MA-macromolecule in aqueous media. MA-hydrogel prepolymers are added in any suitable aqueous solution (including but not limited to PBS, distilled water, or other physiological media) and heated at certain temperature until acquiring a clear hydrogel solution.

In embodiment, the heating temperature is preferably 40-80° C. for gelMA, 60-80° C. for HAMA, below 37° C. for ColMA. The heating time can be varied from 5 min to 12 hours, preferably 5-30 min for gelMA and HAMA, 1-12 hours for ColMA.

Mix the MA-NP and the photoinitiator into the dissolved hydrogel solution in (a). MA-NP and photoinitiator are added to the dissolved the MA-macromolecule solution and incubate within the mixture for a period at 4° C.

In embodiment, the incubation time is preferably 0.5 hour to 7 days, more preferably 1-24 hour in the first and second example.

The bioink can be loaded into molds in this step to form certain shape. Alternatively, the bioink can be redissolved into liquid phase before next step if they are thermally gelated during the incubation.

Photocrosslink the bioink. The bioink in (b) is exposed to energy source, e.g., UV light for a period time to induce photocrosslinking.

The UV light intensity can be varied from 2-30 mW/cm$^2$ or higher (higher than 30 mW/cm$^2$ cannot be measured a specific value) at 320-390 nm wavelength range.

The UV exposure time can be varied between 0.5 min to 24 hours. In some embodiments, where cells are mixed in the bioink, the time is preferably less than 4 hours.

The crosslinking parameters used for bioink depend on the required hydrogel properties, (hydrogel network, mechanical, degradation properties, etc.). UV exposure time can be reduced if the concentration of initiator or the UV intensity is increased.

Example 7: Preparation of GelMA-AuMA NP Hydrogel

GelMA with a degree of methacryloyl substitution >75-80% was used herein. Lyophilized gelMA powder was reconstituted in PBS at 40% w/v and heating to 60° C. as stock solution. GelMA-Au NP prepolymer solutions were prepared by mixing appropriate volumes of the gelMA prepolymer solution with AuMA NPs, at 60° C. and vortexing for 2 min. GelMA and gelMA-Au NP prepolymer solutions comprising 10 or 20% w/v gelMA and 0-37 mM Au NPs were supplemented with 0.5-1.0% w/v Irgacure 2959 or lithium phenyl-2,4,6-trimethylbenzoylphosphinate (LAP) photoinitiator and incubated for 1 h, 24 h, or 7 d at 4° C. Prepolymer solutions with photoinitiator were redissolved before loading into cylindrical molds (4.78 mm inner diameter, 3 mm height) and photocrosslinked under an ultra-violet (UV) light source (320-390 nm) at 7, 15 or 30 mW/cm$^2$ for 4-6 min at ambient temperature. After initial investigations to optimize the above photocrosslinking parameters, all gelMA and gelMA-Au NP hydrogels were prepared with 20% w/v gelMA and up to 37 mM Au NPs by incubating prepolymer solutions with 0.5% w/v LAP photoinitiator for 24 h at 4° C. and photocrosslinking under UV irradiation at 30 mW/cm$^2$ for 4 min.

GelMA hydrogels prepared with AuMA NPs in one-step during photocrosslinking exhibited a linear increase in X-ray attenuation with increased Au NP concentration to enable quantitative imaging by contrast-enhanced micro-CT.

Figure 10:
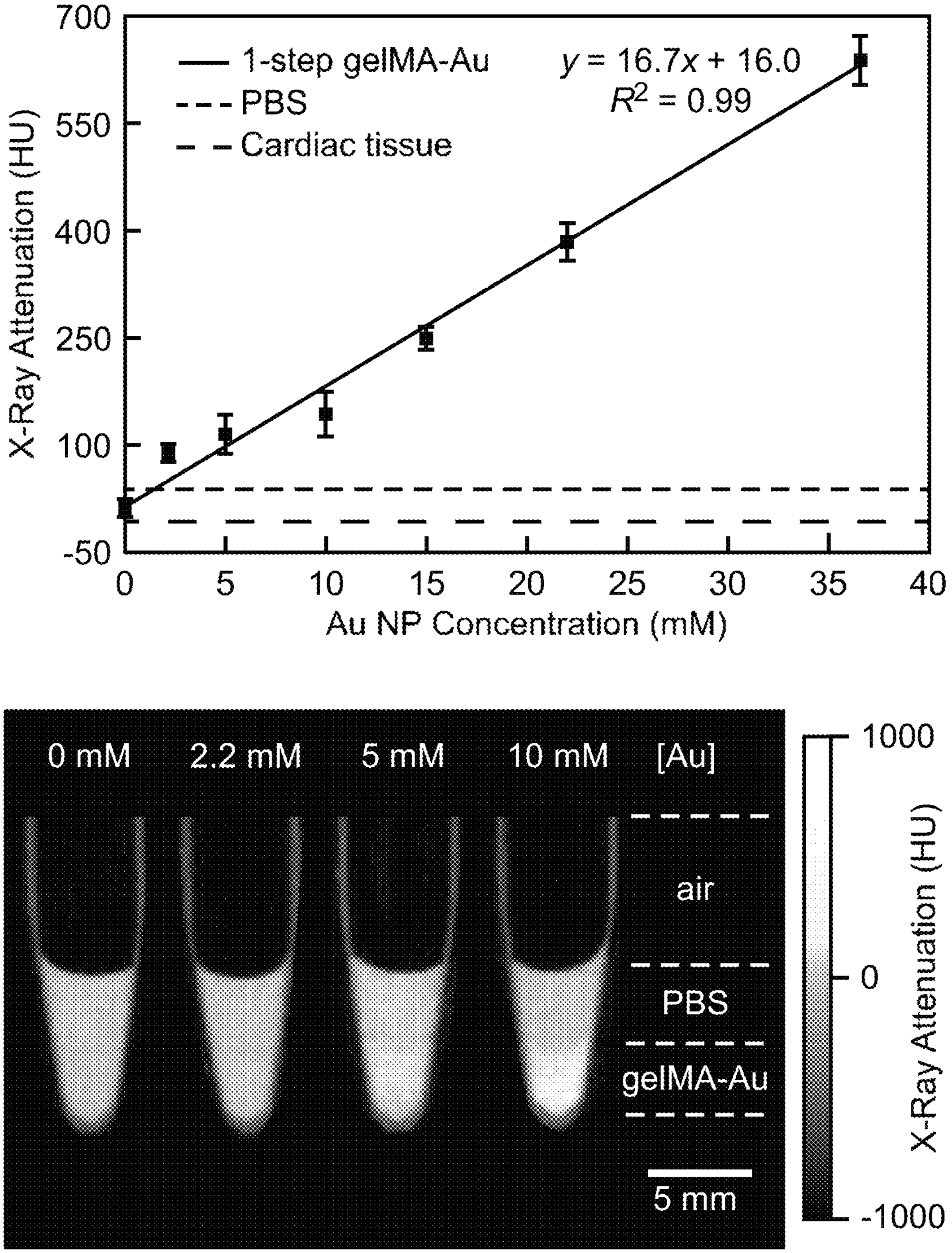
FIG. 10 shows a graph and a micro-computed tomography (micro-CT) image slice that demonstrate X-ray attenuation of hydrogels formed according to the disclosure.

Referring again to the drawings, FIG. 10 shows a graph and micro-CT image slices that demonstrate X-ray attenuation of hydrogels formed according to the disclosure. As depicted, the drawing represents results obtained with an embodiment of the invention for providing radiographic contrast in hydrogels prepared by one-step photocrosslinking with gelMA and methacrylate-modified gold nanoparticles (AuMA NPs). The X-ray attenuation of the hydrogels is shown compared with soft tissue, as represented by phosphate buffered saline (PBS, 38.3 HU) and rat myocardial tissue (−9.3 HU). The measured X-ray attenuation increased linearly with increased AuMA NP concentration ($p<0.001$) and was strongly correlated ($R^2=0.99$). Error bars show one standard deviation of the mean (n=3/concentration). Corresponding grayscale micro-CT images showed that hydrogels containing at least 5 mM Au NPs exhibited visibly greater X-ray attenuation compared with PBS.

The enzymatic and hydrolytic degradation kinetics of gelMA-Au NP hydrogels were longitudinally monitored by micro-CT for up to one month in vitro, and were consistent with concurrent measurements by gravimetric analysis and optical spectroscopy.

Figure 11:
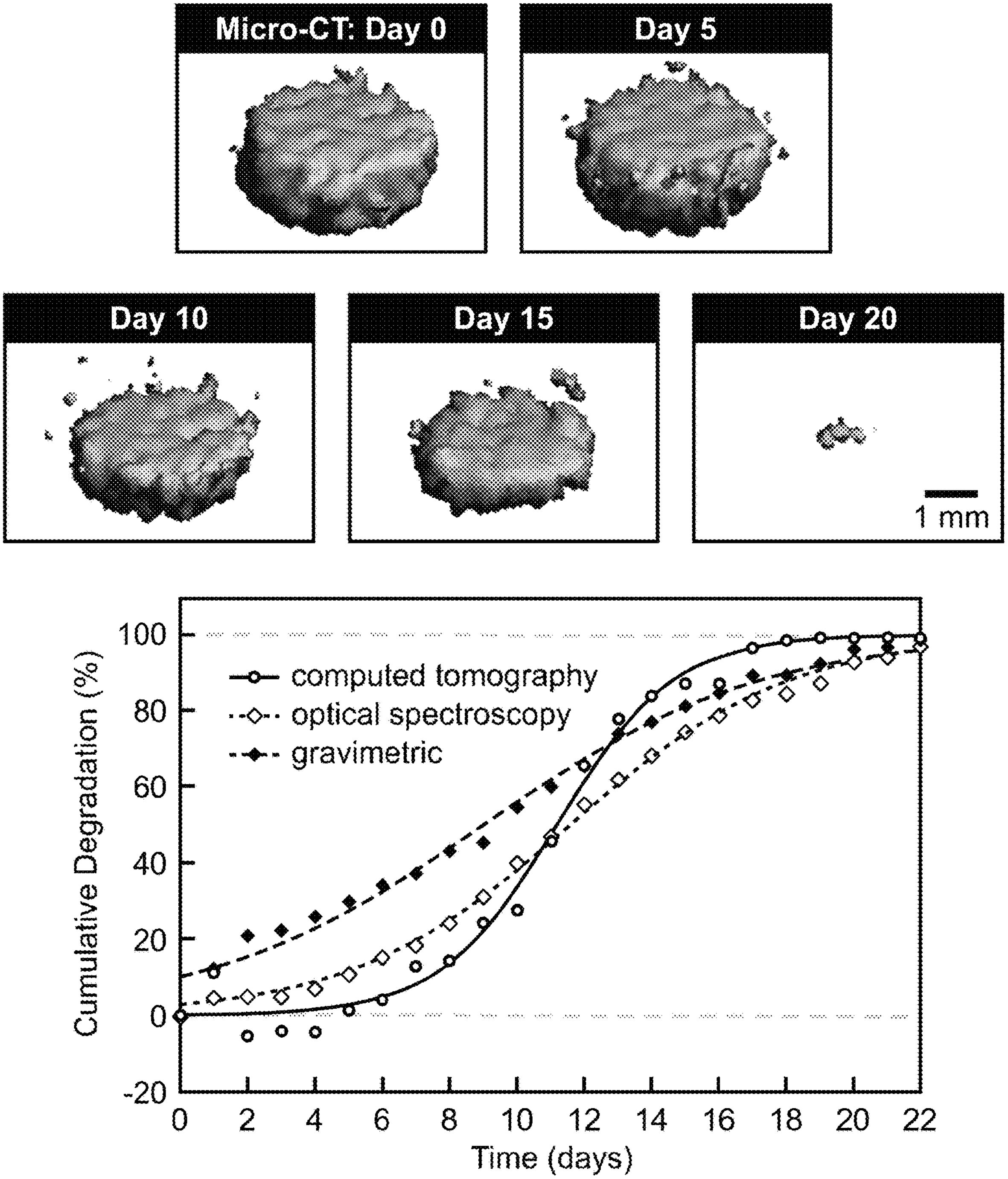
FIG. 11 shows a series of representative segmented micro-CT image reconstructions and a graph demonstrating degradation kinetics of hydrogels formed according to the disclosure.

Referring again to the drawings, FIG. 11 shows a series of representative segmented micro-CT image reconstructions and a graph demonstrating degradation kinetics of hydrogels formed according to the disclosure. As depicted, the drawing represents results obtained with an embodiment of the invention for enabling non-invasive, longitudinal monitoring of enzymatic degradation in hydrogels prepared by one-step photocrosslinking with gelMA and methacrylate-modified gold nanoparticles (AuMA NPs), ~12 nm in size, using contrast-enhanced micro-CT. Representative segmented micro-CT image reconstructions for selected time points show the volume loss of hydrogels with time during enzymatic degradation. Degradation kinetics were measured longitudinally in vitro by the cumulative change in segmented hydrogel volume using contrast-enhanced micro-CT, the cumulative release of Au NPs into the media using optical spectroscopy (ICP-OES), and the cumulative hydrogel mass loss using gravimetric analysis. The degradation kinetics measured non-invasively by micro-CT were strongly correlated (r>0.92, Pearson) with that measured invasively ICP-OES and gravimetric analysis, demonstrating the feasibility of contrast-enhanced micro-CT for non-invasive monitoring of gelMA-Au NP hydrogel degradation. Error bars show one standard deviation of the mean (n=5/group).

Figure 12:
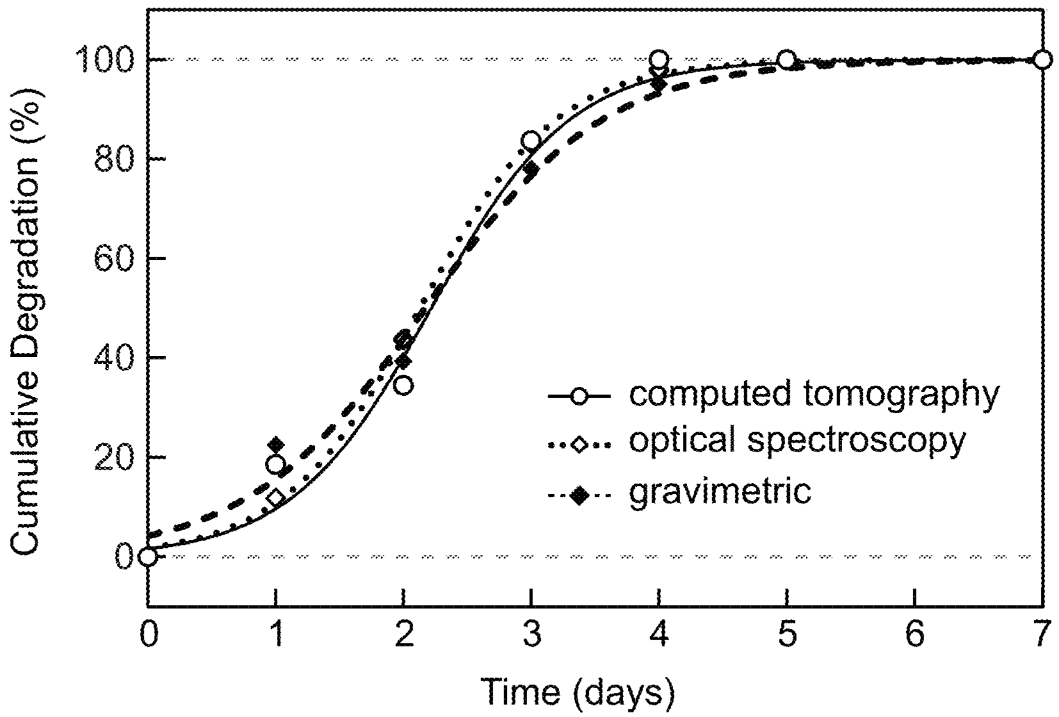
FIG. 12 shows a graph demonstrating degradation kinetics of hydrogels formed according to the disclosure.

Referring again to the drawings, FIG. 12 shows a series of representative segmented micro-CT image reconstructions and a graph demonstrating degradation kinetics of hydrogels formed according to the disclosure. As depicted, the drawing represents results obtained with an embodiment of the invention for enabling non-invasive, longitudinal monitoring of enzymatic degradation in hydrogels prepared by one-step photocrosslinking with gelMA and methacrylate-modified gold nanoparticles (AuMA NPs), ~5 nm in size, using contrast-enhanced micro-CT. Representative segmented micro-CT image reconstructions for selected time points show the volume loss of hydrogels with time during enzymatic degradation. Degradation kinetics were measured longitudinally in vitro by the cumulative change in segmented hydrogel volume using contrast-enhanced micro-CT, the cumulative release of Au NPs into the media using optical spectroscopy (ICP-OES), and the cumulative hydrogel mass loss using gravimetric analysis. The degradation kinetics measured non-invasively by micro-CT were strongly correlated (r>0.99, Pearson) with that measured invasively ICP-OES and gravimetric analysis, demonstrating the feasibility of contrast-enhanced micro-CT for non-invasive monitoring of gelMA-Au NP hydrogel degradation. Error bars show one standard deviation of the mean (n=5/group).

Importantly, gelMA hydrogels prepared with AuMA NPs maintained the unchanged hydrogel network, rheology, and mechanical properties compared with gelMA alone. GelMA hydrogels prepared with AuMA NPs were able to be printed into well-defined three-dimensional (3D) architectures supporting endothelial cell viability.

Example 8: Preparation of HAMA-AuMA NP Hydrogel

HAMA-Au NP hydrogels were prepared with AuMA NPs by one-step photocrosslinking to demonstrate the use of AuMA NPs in other photocrosslinkable hydrogels. HAMA with a DoF of 20-50% and molecular weight of 50,000-70,000 HAMA (Sigma-Aldrich) was dissolved in DPBS at 80° C. to obtain a 10% w/v HAMA prepolymer solution. HAMA and HAMA-Au NP prepolymer solutions comprising 5% w/v HAMA, 10 mM AuMA NPs, and 0.5% w/v LAP photoinitiator were prepared by mixing the HAMA prepolymer solution with AuMA NPs, vortexing for 2 min, adding LAP, and incubating for 24 h at 4° C. Cylindrical hydrogels were prepared by loading the prepolymer solutions into molds (4.78 mm inner diameter, 3 mm height) and photocrosslinking under UV irradiation (320-390 nm) at 30 mW/cm$^2$ for 4 min.

The hydrolytic degradation of HAMA-Au NP hydrogels was longitudinally monitored in vitro by micro-CT for 28 days, and exhibited similar trend as measured by ICP-OES and gravimetric analysis. HAMA-Au hydrogels showed hydrolytic stability for two weeks, but a slight degradation was observed on day 28. These results indicated that HAMA-Au NP hydrogels prepared by the one-step photocrosslinking strategy can be non-invasively monitored during in vitro hydrolysis.

Example 9: Preparation of 3D Printed GelMA-AuMA NP Scaffold

Figure 13:
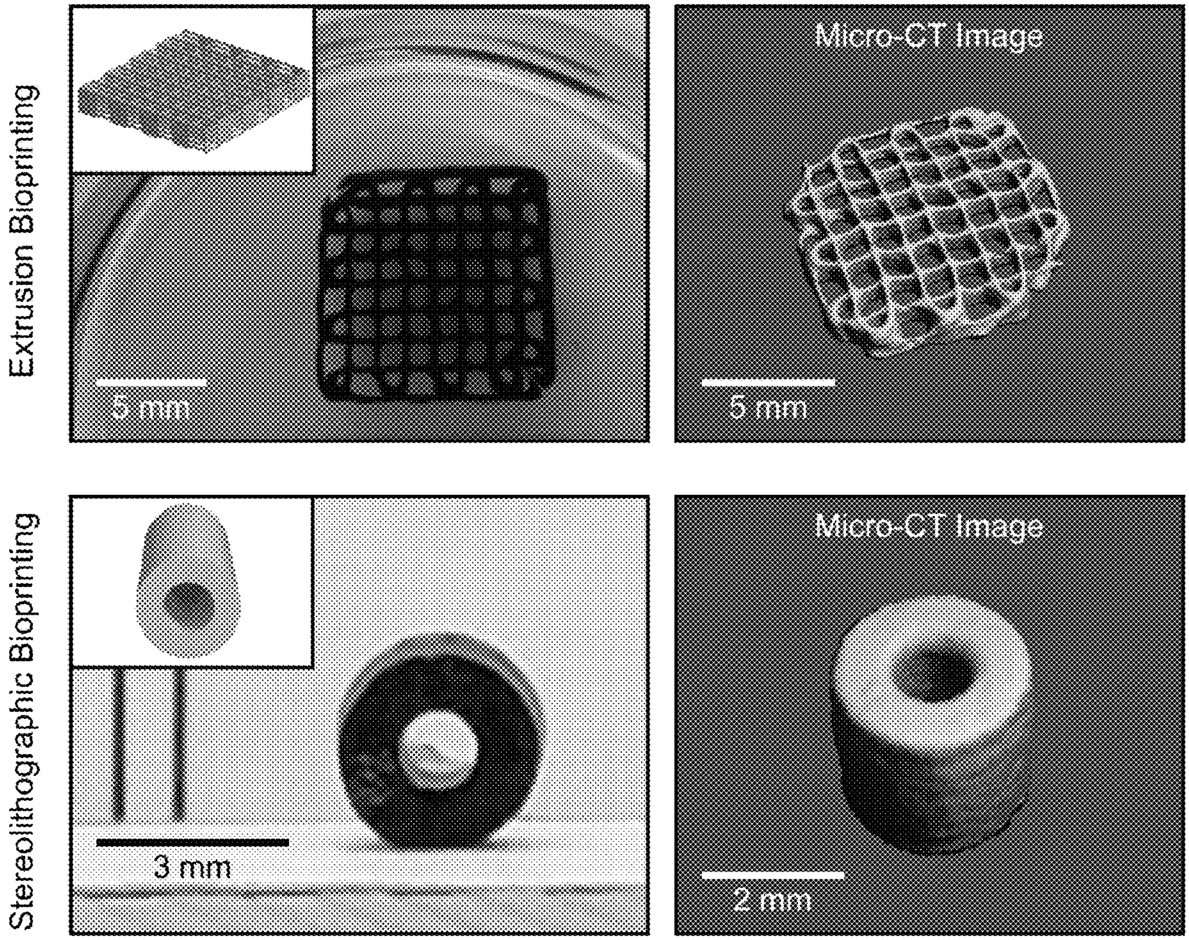
FIG. 13 shows color photographs, inset corresponding CAD models, and corresponding micro-CT image reconstructions for embodiments of photocrosslinked materials prepared according to the disclosure.

Referring again to the drawings, FIG. 13 shows color micro-CT images and inset corresponding CAD models for embodiments of photocrosslinked materials prepared according to the disclosure. As depicted, the drawing represents results obtained with an embodiment of the invention for enabling 3D bioprinting of bioinks comprising gelMA and methacrylate-modified gold nanoparticles (AuMA NPs) which are subsequently photocrosslinked to prepared hydrogel constructs, including a 10-layer lattice scaffold printed by embedded extrusion and a cylindrical tube mimicking a blood vessel printed by stereolithographic bioprinting. Insets show corresponding CAD models. Segmented micro-CT image reconstructions show feasibility of non-invasive radiograph imaging.

While various inventive aspects, concepts and features of the general inventive concepts are described and illustrated herein in the context of various exemplary embodiments, these various aspects, concepts, and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts, and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated.

As used herein, the singular forms “a,” “an,” and “the” are intended to include the plural forms as well, unless the context clearly indicates otherwise. Unless otherwise indicated, all numbers expressing quantities, properties, and so forth as used in the specification and claims are to be understood as being modified in all instances by the term “about.” Accordingly, unless otherwise indicated, the numerical properties set forth in the specification and claims are approximations that may vary depending on the suitable properties desired in embodiments of the present invention.

All ranges and amounts given herein are intended to include subranges and amounts using any disclosed point as an end point. Similarly, a range given of “about 1 to 10 percent” is intended to have the term “about” modifying both the 1 and the 10 percent endpoints, and meaning within 10 percent of the indicated number (e.g. “about 10 percent” means 9-11 percent and “about 2 percent” means 1.8-2.2 percent). Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements. Thus, while exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated. Further, while disclosed benefits, advantages, and solutions to problems have been described with reference to specific embodiments, these are not intended to be construed as essential or necessary to the invention.

The above description is only illustrative of the preferred embodiments which achieve the objects, features and advantages of the present invention. It is not intended that the present invention be limited to the illustrated embodiments. While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiment disclosed as the best mode contemplated for carrying out this invention, but that the invention will include all embodiments falling within the scope of the appended claims.

The invention claimed is:

1. A photocrosslinkable agent comprising:

a. at least one water-soluble methacrylate-modified nanoparticle (100) comprising:

i. a nanoparticle; and ii. a plurality of molecules attached to a surface of the nanoparticle, each of the plurality of molecules comprising a nanoparticle surface attachment ligand (1), a first portion of the plurality of molecules including a terminal methacrylate ligand (103), and a second portion of the plurality of molecules including a hydrophilic terminal ligand (2), wherein any one of the plurality of molecules may include more than one nanoparticle surface attachment ligand and more than one terminal ligand.

2. The photocrosslinkable agent according to claim 1, wherein the nanoparticle surface attachment ligand (1) is selected from the group consisting of thiols, amines, alcohols, silanes, carboxylates, phosphonates, and combinations thereof, and wherein the hydrophilic terminal ligand (2) is selected from the group consisting of thiols, amines, alcohols, carboxylates, silanes, phosphonates, acrylates, epoxides, and combinations thereof.

3. The photocrosslinkable agent according to claim 1, wherein the methacrylate-modified nanoparticle (100) has water solubility that is controlled by the relative amounts of the terminal methacrylate ligand (103) and the hydrophilic terminal ligand (2).

4. The photocrosslinkable agent according to claim 1, wherein the nanoparticles have a shape selected from the group consisting of nanospheres, nanorods, nanoplates, nanoshells, nanotubes, nanocages, nanostars, and combinations thereof, and wherein the nanoparticles are composed of at least one material selected from the group consisting of a metal, a ceramic, a semiconductor, a polymer, and combinations thereof, or wherein the nanoparticles are composed of a combination of at least two materials selected from the group consisting of a metal, a ceramic, a semiconductor, and a polymer, each material forming at least a portion of the nanoparticle, or wherein the nanoparticles have a core-shell structure or a Janus structure.

5. The photocrosslinkable agent according to claim 1, wherein the nanoparticles are composed of a metal or a metal portion, the metal or metal portion of the nanoparticle selected from the group consisting of magnesium, aluminum, titanium, vanadium, chromium, manganese, iron, cobalt, nickel, nitinol, copper, zinc, selenium, zirconium, molybdenum, palladium, silver, gadolinium, tantalum, tungsten, iridium, platinum, gold, bismuth, and alloys and combinations thereof.

6. The photocrosslinkable agent according to claim 1, wherein the nanoparticles are composed of a ceramic or a ceramic portion, the ceramic or ceramic portion of the nanoparticle selected from the group consisting of boron nitride, magnesium oxide, aluminum oxide, aluminum nitride, silicon dioxide, silicon nitride, titanium dioxide, titanium carbide, hematite or iron(III) oxide, magnetite or iron(II,III) oxide, copper oxide, zinc oxide, strontium titanate, zirconium oxide, cerium oxide, gadolinium oxide, tantalum oxide, barium titanate, barium sulfate, hafnium oxide, tungsten oxide, hydroxyapatite, calcium-deficient hydroxyapatite, carbonated calcium hydroxyapatite, beta-tricalcium phosphate, alpha-tricalcium phosphate, amorphous calcium phosphate, octacalcium phosphate, tetracalcium phosphate, biphasic calcium phosphate, anhydrous dicalcium phosphate, dicalcium phosphate dihydrate, anhydrous monocalcium phosphate, monocalcium phosphate monohydrate, calcium silicates, calcium aluminates, calcium carbonate, calcium sulfate, zinc phosphate, zinc silicates, aluminosilicates, zeolites, bioglass 45, bioglass 52S4.6, and combinations thereof.

7. The photocrosslinkable agent according to claim 1, wherein the nanoparticles are composed of a semiconductor or a semiconductor portion, the semiconductor or semiconductor portion of the nanoparticle selected from the group consisting of silicon, graphene, zinc oxide, zinc sulfide, zinc selenide, gallium arsenide, cadmium oxide, cadmium sulfide, cadmium selenide, and combinations thereof.

8. The photocrosslinkable agent according to claim 1, wherein the nanoparticles are composed of a polymer or a polymer portion, the polymer or polymer portion of the nanoparticle selected from the group consisting of polyaryletherketone (PAEK), polyetheretherketone (PEEK), polyetherketonekteone (PEKK), polyetherketone (PEK), polytetrafluoroethylene (PTFE) polyethylene, high density polyethylene (HDPE), ultra-high molecular weight polyethylene (UHMWPE), low density polyethylene (LDPE), polyethylene oxide (PEO), polyethylene terephthalatepolyurethane (PET), polypropylene, polypropylene oxide (PPO), polysulfone, polyethersulfone, polyphenylsulfone, poly(vinyl chloride) (PVC), polyoxymethylene, polyacrylonitrile (PAN), polystyrene, poly(vinyl alcohol) (PVA), poly(DL-lactide) (PDLA), poly(L-lactide) (PLLA), poly(glycolide) (PGA), poly(ε-caprolactone) (PCL), poly(dioxanone) (PDO), poly(glyconate), poly(hydroxybutyrate) (PHB), poly (hydroxyvalerate (PHV), poly(orthoesters), poly(carboxylates), poly(propylene fumarate), poly(phosphates), poly (carbonates), poly(anhydrides), poly(iminocarbonates), poly (phosphazenes), polyimides, polyamides, polysiloxanes, polyphosphates, citric-acid based polymers, polyacrylics, polymethylmethacrylate (PMMA), bisphenol A-glycidyl methacrylate (bis-GMA), tri(ethylene glycol) dimethacrylate (TEG-DMA), poly(2-hydroxyethyl methacrylate) (HEMA)poly(acrylic acid) (PAA), polyethylene glycol (PEG), polysaccharides, gelatin, collagen, alginate, chitosan, dextran, carboxymethyl cellulose, polypeptides, copolymers thereof, and combinations thereof.

9. A photocrosslinkable ink for forming a material or structure, comprising:

a. a suitable solvent comprising water;

b. a plurality of water-soluble methacrylate-modified nanoparticles, each of the methacrylate-modified nanoparticles comprising:

i. a nanoparticle; and ii. a plurality of molecules attached to a surface of the nanoparticle, each of the plurality of molecules comprising a nanoparticle surface attachment ligand (1) and at least a portion of the plurality of molecules comprising a terminal methacrylate ligand (103); and at least a portion of the molecules comprising a hydrophilic terminal ligand (2), wherein any one of the plurality of molecules may include more than one nanoparticle surface attachment ligand and more than one terminal ligand, c. optionally, a plurality of methacrylate-modified macromolecules (107); and d. a photoinitiator.

10. The photocrosslinkable ink according to claim 9 comprising the plurality of methacrylate-modified macromolecules (107), wherein the plurality of methacrylate-modified macromolecules (107) is selected from the group consisting of polymers, oligomers or a combination thereof selected from the group consisting of gelatin-methacrylate (gelMA), collagen-methacrylate (colMA), alginate-methacrylate (algMA), hyaluronic acid-methacrylate (HAMA), dextran-methacrylate (dexMA), chitosan-methacrylate (chiMA), chondroitin sulfate-methacrylate (CSMA), heparin-methacrylate (hepMA), carboxymethyl cellulose-methacrylate (CMCMA), polyethylene glycol dimethacrylate (PEGDA), polyurethane-methacrylate, polyacrylic acid (PAA), polymethyl methacrylate (PMMA), poly(2-hydroxyethyl methacrylate) (HEMA), bisphenol A-glycidyl methacrylate (bis-GMA), tri(ethylene glycol) dimethacrylate (TEG-DMA), diethyleneglycol diacrylate (DEGDA), and combinations thereof.

11. The photocrosslinkable ink according to claim 9, wherein the methacrylate-modified nanoparticle (100) has water solubility that is controlled by the relative amounts of the terminal methacrylate ligand (103) and the hydrophilic terminal ligand (2).

12. A photocrosslinked material comprising the photocrosslinkable agent-according to claim 1, comprising:

(i) a plurality of water-soluble methacrylate-modified nanoparticles, wherein at least a portion of the plurality of the terminal methacrylate ligands (103) on the nanoparticles (101) are photocrosslinked, resulting in a covalent linkage (109) between the methacrylate-modified nanoparticles (100);

(ii) at least one water-soluble methacrylate-modified nanoparticle (100) and a plurality of water-soluble methacrylate-modified macromolecules (107), wherein at least a portion of the plurality of the terminal methacrylate ligands (103) on the at least one nanoparticle are photocrosslinked with at least a portion of the methacrylate-modified macromolecules (107), the photocrosslinked material comprising a covalent linkage between the photocrosslinked methacrylate-modified nanoparticles (100) and methacrylate-modified macromolecules (107); or (iii) a combination of (i) and (ii).

13. The photocrosslinked material according to claim 12, wherein the photocrosslinked material comprises a plurality of methacrylate-modified macromolecules (107), and the photocrosslinked material exhibits at least one or more properties selected from the group consisting of crosslinking density, rheology, mechanical stiffness, mechanical strength, swelling, degradation kinetics, and any combination thereof, and wherein at least one or more of the properties are not substantially altered by the presence of the photocrosslinkable agent as compared to a photocrosslinked product formed by photocrosslinking the methacrylate-modified macromolecules (107) in the absence of the photocrosslinkable agent.

14. A method for providing a photocrosslinkable agent, the method comprising:

a. providing a nanoparticle;

b. providing a first bifunctional molecule (105) comprising a nanoparticle surface attachment ligand (1) that is attached to a surface of the nanoparticle, and a terminal ligand comprising a hydrophilic terminal ligand (2) capable of covalent linking to a terminal ligand of another molecule;

c. providing a second bifunctional molecule (106) comprising a terminal methacrylate ligand (103) and a terminal ligand comprising a coupling ligand (4) capable of covalent linking to the hydrophilic terminal ligand (2) of the first molecule; and d. covalently linking the hydrophilic terminal ligand (2) of the first molecule to the coupling ligand (4) of the second molecule, optionally in the presence of a coupling agent or catalyst, forming a water-soluble methacrylate-modified nanoparticle, wherein any one of the first, second or both first and second bifunctional molecules may include more than one nanoparticle surface attachment ligand and more than one terminal ligand.

15. The method of claim 14, wherein covalent linking to the coupling ligand (4) of the second molecule is carried out under conditions that result in incomplete conversion of the hydrophilic terminal coupling ligands (2) such that the nanoparticle is surface functionalized with a conjugated molecule comprising a nanoparticle surface attachment ligand (1) and a terminal methacrylate ligand (103), and the first molecule comprising the nanoparticle surface attachment ligand (1) and hydrophilic terminal ligand (2), and wherein the methacrylate-modified nanoparticle (100) has a water solubility that is controlled by the relative amounts of the conjugated molecule and the first molecule.

16. The photocrosslinked material according to claim 12, wherein the photocrosslinked material is photocrosslinked at a frequency in the range from ultraviolet to near-infrared and an intensity in a range from 2 to 30 $mW/cm^2$ for 0.5 min to 24 hours.

17. The method for providing a photocrosslinkable agent according to claim 14, wherein:

a. the first bifunctional molecule (105) comprises a carboxylate terminal ligand as the hydrophilic terminal ligand (2);

b. the second bifunctional molecule (106) comprises a terminal amine coupling ligand (4) capable of covalent linking to the carboxylate terminal group of the hydrophilic terminal ligand (2) of the first bifunctional molecule; and c. covalently linking the hydrophilic terminal ligand (2) of the first bifunctional molecule to the terminal coupling ligand (4) of the second bifunctional molecule, in the presence of 1-ethyl-3-(3-dimethylaminopropyl) carbodiimide hydrochloride (EDC) and N-hydroxysuccinimide or N-hydroxysulfosuccinimide (NHS) in alcohol, wherein a molar ratio of EDC:NHS:MA is in a range of 15:6:6 to 50:20:20.

18. The photocrosslinkable agent according to claim 1, wherein the nanoparticles are composed of a noble metal.

19. The method according to claim 17, wherein the total time for the coupling reaction, which influences the degree of methacrylation and hydrophilicity of the methacrylate-modified nanoparticles, is from 3 to 48 h.

20. The method according to claim 17, wherein the coupling reaction pH between 4.0-8.5.

* * * * *